(12) United States Patent
Spence et al.

(10) Patent No.: US 10,610,653 B2
(45) Date of Patent: Apr. 7, 2020

(54) GAS THERAPY SYSTEM PROVIDING POSITIVE AND NEGATIVE GAS FLOWS

(71) Applicant: Fisher & Paykel Healthcare Limited, Auckland (NZ)

(72) Inventors: Callum James Thomas Spence, Auckland (NZ); John Whitney Storey, Auckland (NZ); Jonathan David Harwood, Auckland (NZ); Quinton Michael Smith, Auckland (NZ); Alicia Jerram Hunter Evans, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 603 days.

(21) Appl. No.: 15/128,734

(22) PCT Filed: Apr. 10, 2015

(86) PCT No.: PCT/NZ2015/050044
§ 371 (c)(1),
(2) Date: Sep. 23, 2016

(87) PCT Pub. No.: WO2015/156690
PCT Pub. Date: Oct. 15, 2015

(65) Prior Publication Data
US 2018/0078719 A1   Mar. 22, 2018
US 2018/0318531 A9   Nov. 8, 2018

Related U.S. Application Data

(60) Provisional application No. 61/978,662, filed on Apr. 11, 2014, provisional application No. 62/034,061, filed on Aug. 6, 2014.

(51) Int. Cl.
A61M 16/00   (2006.01)
A61M 16/16   (2006.01)
(Continued)

(52) U.S. Cl.
CPC .... *A61M 16/0009* (2014.02); *A61M 16/0057* (2013.01); *A61M 16/0069* (2014.02);
(Continued)

(58) Field of Classification Search
CPC .......... A61M 16/0009; A61M 16/0069; A61M 16/009; A61M 16/0666; A61M 16/0672;
(Continued)

(56) References Cited

U.S. PATENT DOCUMENTS 2,429,474 A * 10/1947 McMahon ............. G01N 25/68
356/446
4,036,210 A * 7/1977 Campbell ......... A61M 16/0463
128/207.16
(Continued)

FOREIGN PATENT DOCUMENTS

EP        1849491          10/2007
WO    WO 2013/142150    9/2013
WO    WO 2015/156690   10/2015

OTHER PUBLICATIONS

International Search Report for PCT/NZ2015/050044 in 5 pages.
Written Opinion for PCT/NZ2015/050044 in 4 pages.

*Primary Examiner* — Kathryn E Ditmer
(74) *Attorney, Agent, or Firm* — Knobbe, Martens, Olson & Bear, LLP

(57) ABSTRACT

A respiratory therapy system configured to deliver gases to a patient can have a non-sealed gas flow generating arrangement configured to deliver a high flow of positive gas to an airway of a patient and a negative flow of gas away from an airway of the patient. The positive and negative flows of gas can be generated simultaneously. The flow of positive and negative gases reduces exhaled gases in anatomical dead spaces of the patient.

19 Claims, 12 Drawing Sheets

(51) Int. Cl.
*A61M 16/06* (2006.01)
*A61M 16/08* (2006.01)
*A61M 16/10* (2006.01)

(52) U.S. Cl.
CPC ...... *A61M 16/024* (2017.08); *A61M 16/0666* (2013.01); *A61M 16/0672* (2014.02); *A61M 16/0677* (2014.02); *A61M 16/08* (2013.01); *A61M 16/16* (2013.01); *A61M 16/109* (2014.02); *A61M 16/161* (2014.02); *A61M 2016/0027* (2013.01); *A61M 2016/0033* (2013.01); *A61M 2016/103* (2013.01); *A61M 2016/1025* (2013.01); *A61M 2205/3368* (2013.01); *A61M 2205/50* (2013.01); *A61M 2206/20* (2013.01); *A61M 2230/06* (2013.01); *A61M 2230/10* (2013.01); *A61M 2230/201* (2013.01); *A61M 2230/202* (2013.01); *A61M 2230/205* (2013.01); *A61M 2230/432* (2013.01); *A61M 2230/435* (2013.01); *A61M 2230/50* (2013.01)

(58) Field of Classification Search
CPC ............ A61M 16/024; A61M 16/0057; A61M 16/16; A61M 16/08
See application file for complete search history.

(56) References Cited

U.S. PATENT DOCUMENTS

| | | | | | |
|---|---|---|---|---|---|
| 4,048,993 | A | * | 9/1977 | Dobritz | A61M 16/1045 128/201.13 |
| 4,151,843 | A | * | 5/1979 | Brekke | A61M 16/0666 128/204.24 |
| 4,248,218 | A | * | 2/1981 | Fischer | A61M 16/009 128/204.18 |
| 4,300,550 | A | * | 11/1981 | Gandi | A61M 16/0463 128/207.18 |
| 4,989,599 | A | * | 2/1991 | Carter | A61M 16/0666 128/204.18 |
| 5,099,836 | A | | 3/1992 | Rowland et al. | |
| 6,379,312 | B2 | * | 4/2002 | O'Toole | A61B 5/0836 600/529 |
| 6,799,575 | B1 | * | 10/2004 | Carter | A61M 16/0666 128/204.18 |
| 6,913,017 | B2 | * | 7/2005 | Roberts | A61M 16/0666 128/206.11 |
| 6,929,007 | B2 | * | 8/2005 | Emerson | A61M 16/0057 128/204.23 |
| 6,986,353 | B2 | * | 1/2006 | Wright | A61M 16/0666 128/200.26 |
| 8,770,199 | B2 | * | 7/2014 | Flanagan | A61M 16/10 128/207.18 |
| 2002/0017300 | A1 | * | 2/2002 | Hickle | A61B 5/0836 128/204.22 |
| 2002/0053346 | A1 | * | 5/2002 | Curti | A61M 16/0666 128/207.18 |
| 2002/0055685 | A1 | * | 5/2002 | Levitsky | A61B 5/083 600/543 |
| 2002/0112730 | A1 | * | 8/2002 | Dutkiewicz | A61M 16/0666 128/207.18 |
| 2003/0051729 | A1 | * | 3/2003 | Be'eri | A61M 16/20 128/204.18 |
| 2004/0103899 | A1 | | 6/2004 | Noble | |
| 2004/0231673 | A1 | * | 11/2004 | Reissmann | A61M 16/04 128/207.14 |
| 2006/0042631 | A1 | * | 3/2006 | Martin | A61B 5/0836 128/207.18 |
| 2006/0130840 | A1 | * | 6/2006 | Porat | A61M 16/0666 128/206.11 |
| 2006/0178592 | A1 | * | 8/2006 | Nason | A61B 5/0803 600/532 |
| 2006/0272643 | A1 | | 12/2006 | Aylsworth et al. | |
| 2007/0186928 | A1 | * | 8/2007 | Be'Eri | A61M 16/00 128/204.18 |
| 2008/0142019 | A1 | * | 6/2008 | Lewis | A61M 16/024 128/207.18 |
| 2008/0190436 | A1 | * | 8/2008 | Jaffe | A61M 16/0666 128/207.18 |
| 2008/0251070 | A1 | * | 10/2008 | Pinskiy | A61B 5/0836 128/202.22 |
| 2010/0122699 | A1 | * | 5/2010 | Birnkrant | A61M 1/0023 128/204.21 |
| 2010/0147302 | A1 | * | 6/2010 | Selvarajan | A61M 16/024 128/204.23 |
| 2010/0229861 | A1 | * | 9/2010 | Nashed | A61M 16/009 128/203.29 |
| 2010/0242622 | A1 | * | 9/2010 | Weckstrom | A61B 5/087 73/861.52 |
| 2011/0094508 | A1 | * | 4/2011 | Carey | A61M 16/01 128/203.14 |
| 2011/0094518 | A1 | | 4/2011 | Cippollone et al. | |
| 2011/0277765 | A1 | * | 11/2011 | Christopher | A61M 16/0051 128/204.17 |
| 2013/0012869 | A1 | * | 1/2013 | Cha | A61M 3/0229 604/28 |
| 2013/0092165 | A1 | * | 4/2013 | Wondka | A61M 15/08 128/204.25 |
| 2013/0104901 | A1 | * | 5/2013 | Landis | A61M 16/0666 128/205.25 |
| 2013/0109992 | A1 | * | 5/2013 | Guyette | A61M 16/06 600/532 |
| 2013/0274651 | A1 | * | 10/2013 | Barbut | A61M 31/00 604/26 |
| 2014/0150791 | A1 | * | 6/2014 | Birnkrant | A61M 16/024 128/204.23 |
| 2015/0020810 | A1 | * | 1/2015 | Stupak | A61M 16/0666 128/205.19 |
| 2015/0099993 | A1 | * | 4/2015 | Weaver | A61M 16/0463 600/531 |
| 2015/0230731 | A1 | * | 8/2015 | Levitsky | A61B 5/097 600/532 |
| 2016/0199603 | A1 | * | 7/2016 | Kawamura | A61M 16/12 128/200.19 |

* cited by examiner

GAS THERAPY SYSTEM PROVIDING POSITIVE AND NEGATIVE GAS FLOWS

INCORPORATION BY REFERENCE TO ANY PRIORITY APPLICATIONS

The present application is a national phase of PCT Application No. PCT/NZ2015/050044, filed Apr. 10, 2015, titled "GAS THERAPY SYSTEM," which claims priority benefit under 35 U.S.C. § 119(e) to U.S. Provisional Patent Application Ser. No. 61/978,662, filed Apr. 11, 2014 titled "GAS THERAPY SYSTEM,"; U.S. Provisional Patent Application Ser. No. 62/034,061, filed Aug. 6, 2014, and any and all applications for which a foreign or domestic priority claim is identified in the Application Data Sheet as filed with the present application. Each of the foregoing are hereby incorporated by reference under 37 CFR 1.57.

FIELD OF THE DISCLOSURE

The present disclosure generally relates to respiratory therapy. More particularly, the present disclosure relates to gas delivery systems for use in respiratory therapy.

BACKGROUND

A patient dealing with respiratory illness, for example chronic obstructive pulmonary disease (COPD), can have difficulty engaging in effective respiration. This difficulty may be the result of a variety of physiological faults, including a breakdown of lung tissue, dysfunctions of the small airways, excessive accumulation of sputum, infection, genetic disorders, or cardiac insufficiency. With such illnesses, it is useful to provide the patient with a therapy that can improve the ventilation of the patient. In some situations, the patient can be provided with a respiratory therapy system that includes a gas source, an interface that may be used to transmit gas to an airway of a patient, and a conduit extending between the gas source and the interface. Gas delivered to an airway of the patient from the gas source can help to promote adequate ventilation of the patient. The gas source may, for example, be a container of air and/or another gas suitable for inspiration, for example, oxygen or nitric oxide, a mechanical blower capable of propelling a gas through the conduit to the interface, or some combination of both. The respiratory therapy system may include structure used to heat and/or humidify gases passing through the system to improve patient comfort and/or improve the prognosis of the patient's respiratory illness.

A patient suffering from respiratory conditions may benefit from reducing the volume of air that he inhales that does not take part in the normal gas exchange of oxygen (O2) and carbon dioxide (CO2). This volume of air is contributed to by anatomical dead space, which is gas that includes exhaled CO2 captured in the patient's airways that is rebreathed upon inspiration. To reduce dead space, the patient can be treated with high flow therapy, which can involve the administration of gas to the airways of a patient at a relatively high flow rate and at a relatively low pressure. The high flow of gases reaching the patient's airways can be beneficial for flushing out the patient's airways, which can reduce the volume of anatomical dead space. High flow therapy is often delivered with an unsealed patient interface such as, for example, a nasal cannula.

It is an object of certain embodiments disclosed herein to provide an improved or alternative system and method for respiratory therapy that might overcome or ameliorate problems with existing systems or methods, or at least provide the public with a useful choice.

SUMMARY

Although high flow therapy may be useful for reducing the level of anatomical dead space in the airways of a patient, the level of dead space clearance may be limited by the flow rate of gases supplied to the patient and/or by the path taken by gases expelled from the patient's airways. For example, if the patient is receiving high flow therapy and is using a nasal cannula, if the patient's mouth is open, exhaled gases may travel up the airways and leave the patient's body through the mouth or through the nares. However, if the patient's mouth is closed, exhaled gases may leave the patient's body substantially through the nares. The level of anatomical dead space present if the patient's mouth is closed may be greater than the level of anatomical dead space present if the patient's mouth is open because the exhaled gases may be required to travel further along the patient's airways to escape the body. Additionally, for some patients, the respiratory effort necessary for inhalation and/or exhalation is difficult to meet. More respiratory effort may be required to force the exhaled gases from the nares relative to the respiratory effort required to force the exhaled gases from both the mouth and nares. This additional respiratory effort may be difficult to achieve for a patient with impaired respiratory function.

Thus, in accordance with certain features, aspects and advantages at least some of the embodiments disclosed herein, a respiratory therapy system is disclosed that provides additional and/or alternative anatomical dead space respiratory clearance assistance. The respiratory therapy system may comprise a non-sealed gas flow generating arrangement. A first gas passageway may be adapted to pneumatically link at least a part of the gas flow generating arrangement to an airway of the patient. A second gas passageway may be adapted to pneumatically link at least a part of the gas flow generating arrangement to an airway of the patient. The gas flow generating arrangement may be configured to simultaneously deliver gases at a positive flow rate through the first gas passageway and draw gases at a negative flow rate through the second gas passageway. The first gas passageway may be substantially pneumatically isolated from the second gas passageway. The negative flow rate can provide additional and/or alternative anatomical dead space clearance. In some embodiments, the negative flow provides additional clearance. In some embodiments, the negative flow allows for a reduction in positive flow without compromising the anatomical dead space clearance. This can provide greater physical comfort to a patient.

In some embodiments, a respiratory therapy system is disclosed. The system has a positive gas flow source, a negative gas flow source, at least one gas passageway adapted to provide a non-sealed pneumatic link between an airway of a patient and the positive and negative gas flow sources, and a hardware controller which controls the positive gas flow source to deliver a positive flow of gas to a subject via the at least one gas passageway and control the negative gas flow source to provide a negative flow of gas configured to draw gas from the airway of a patient at a sufficient flow rate to reduce a concentration of an exhaled gas in a physiological dead space of a subject. In some embodiments, the positive gas flow source and the negative gas flow source are provided simultaneously. In some embodiments, the positive flow of gas comprises a rate of at least 10 liters per minute. In some embodiments, the positive flow of gas comprises a rate of about 20 liters per minute to about 40 liters per minute. In some embodiments, the negative flow of gas comprises a rate of at least 0.5 liters per minute. In some embodiments, the negative flow of gas comprises a rate that is at least 25% of a rate of the positive flow of gas. In some embodiments, the system comprises a first gas passageway adapted to provide a non-sealed pneumatic link between an airway of a patient and the positive gas flow source and a second gas passageway adapted to provide a non-sealed pneumatic link between an airway of a patient and the negative gas flow source. In some embodiments, the first and second gas passageways are both in a single conduit. In some embodiments, the first gas passageway is in a first conduit and the second gas passageway is in a second conduit. In some embodiments, the first gas passageway interfaces with a first patient interface and the second gas passageway interfaces with a second patient interface. In some embodiments, the first patient interface is a nasal interface and the second patient interface is an oral interface, or wherein the first patient interface is an oral interface and the second patient interface is a nasal interface. In some embodiments, the first gas passageway and the second gas passageway interface with a patient interface that substantially maintains pneumatic isolation of the positive and negative flows of the first gas passageway and the second gas passageway. In some embodiments, the patient interface is a nasal cannula. In some embodiments, the nasal cannula comprises a first nasal prong and a second nasal prong, the first and second nasal prongs adapted to be fitted into the nares of the patient, and a manifold in pneumatic communication with the nasal prongs, the first gas passageway, and the second gas passageway. In some embodiments, a first side of the manifold accepts the first gas passageway, and wherein a second side of the manifold accepts the second gas passageway. In some embodiments, the first gas passageway extends into the first nasal prong and the second gas passageway extends into the second nasal prong. In some embodiments, both the first and second gas passageways extend into each of the first nasal prong and the second nasal prong. In some embodiments, both the first and second gas passageways enter the manifold on a single side of the manifold. In some embodiments, also includes a humidifier adapted to heat and/or humidify gases passing through the first gas passageway. In some embodiments, the system also has a transfer module configured to transfer moisture and/or heat from the second gas passageway to the first gas passageway. In some embodiments, the transfer module comprises a wick or absorbent material. In some embodiments, non-sealed pneumatic link comprises an occlusion of less than 95% of the airway of the patient. In some embodiments, the non-sealed pneumatic link comprises an occlusion of less than 90% of the airway of the patient. In some embodiments, the non-sealed pneumatic link comprises an occlusion of between 40% and 80% of the airway of the patient. In some embodiments, the airway is one or more of a nare or mouth. In some embodiments, the non-sealed pneumatic link delivers 1 cm or less of pressure per 10 L/min of flow. In some embodiments, the non-sealed pneumatic link delivers 1 cm or less of pressure per 15 L/min of flow.

A method of delivering gas to the airway of a subject in need thereof is also disclosed. The method improves the ventilation of a subject in need thereof, reducing the volume of anatomical dead space within the volume of the airway of a subject in need thereof, and/or treating a respiratory condition or a sleep disorder in a subject in need thereof. The method can include providing a positive gas flow source, delivering, using the positive gas flow source, a continuous flow of positive gas to the airway of a subject via at least one gas passageway adapted to provide a non-sealed pneumatic link between an airway of a patient and the positive gas flow source, providing a negative gas flow source, and drawing gas, using the negative gas flow source, from the airway of the subject at a flow rate sufficient to reduce a concentration of an exhaled gas in a physiological dead space of a subject's airways. In some embodiments, the delivering and the drawing are performed simultaneously. In some embodiments, the delivering the continuous flow of gas comprises delivering a positive flow of gas at a rate of at least 10 liters per minute. In some embodiments, the delivering the continuous flow of gas comprises delivering a positive flow of gas at a rate of at least 20 liters per minute. In some embodiments, drawing gas using the negative flow source comprises drawing gas at a rate of at least 0.5 liters per minute. In some embodiments, drawing gas using the negative flow source comprises drawing gas at a rate of at least 25% of a rate of the positive glow of gas. In some embodiments, gas is delivered to the airway of the subject through a first gas passageway and gas is drawn from the airway of the subject through a second gas passageway that is substantially pneumatically isolated from the first gas passageway. In some embodiments, the first and second gas passageways are pneumatically connected to one or more patient interfaces that substantially maintain the pneumatic isolation of the flow of gas in each passageway. In some embodiments, the first and second gas passageways are in separate conduits or a single conduit. In some embodiments, gas is delivered to the airway of the subject through a first patient interface and gas is drawn from the airway of the subject through a second patient interface. In some embodiments, gas is delivered to the airway of the subject through a first patient interface and gas is drawn from the airway of the subject through the same patient interface. In some embodiments, the first patient interface is a nasal interface and the second patient interface is an oral interface, or the first patient interface is an oral interface and the second patient interface is a nasal interface. In some embodiments, the first patient interface is a nasal interface or an oral interface. In some embodiments, the nasal interface is a nasal cannula. In some embodiments, the nasal interface is a nasal cannula. In some embodiments, the nasal cannula comprises a first nasal prong that delivers a continuous flow of gas to the airway and a second nasal prong that simultaneously draws gas from the airway. In some embodiments, the nasal cannula comprises a first nasal prong and a second nasal prong, each nasal prong delivering a continuous flow of gas to the airway and simultaneously drawing gas from the airway. In some embodiments, the subject's mouth is closed or sealed. In some embodiments, the subject's mouth is open. In some embodiments, the gas pressure in the subject's airway is measured. In some embodiments, the gas pressure in the subject's airway is maintained at a level of less than about 4 cm H2O, preferably at a level of less than about 3.5, 3, 2.5, 5 or 1 cm H2O, preferably with the subject's mouth open or closed, preferably with the subject's mouth closed. In some embodiments, the oxygen concentration of the subject's airway is measured. In some embodiments, the oxygen concentration of the subject's airway is maintained at a substantially constant level or increased. In some embodiments, the carbon dioxide concentration of the subject's airway is measured. In some embodiments, the carbon dioxide concentration of the subject's airway is maintained at a substantially constant level or reduced. In some embodiments, the molar fraction of carbon dioxide in the upper airway of the subject is reduced by at least about 10 molar % compared to the molar fraction of carbon dioxide in the upper airway of the subject when breathing without assistance. In some embodiments, wherein the molar fraction of carbon dioxide in the upper airway of the subject is reduced by at least about 1 molar % compared to nasal high flow therapy conducted at an equivalent flow rate when the subject's mouth is open. In some embodiments, wherein the molar fraction of carbon dioxide in the upper airway of the subject is reduced by at least about 10 molar % compared to nasal high flow therapy conducted at an equivalent flow rate when the subject's mouth is closed. In some embodiments, the peripheral capillary oxygen saturation of the subject is measured. In some embodiments, the peripheral capillary oxygen saturation of the subject is maintained at a substantially constant level or increased. In some embodiments, the peripheral capillary oxygen saturation of the subject is increased compared to nasal high flow therapy conducted at an equivalent flow rate. In some embodiments, the non-sealed pneumatic link provides less than 95% occlusion of the airway of the patient. In some embodiments, the non-sealed pneumatic link provides less than 90% occlusion of the airway of the patient. In some embodiments, the non-sealed pneumatic link provides between 40% and 80% occlusion of the airway of the patient. In some embodiments, the airway is one or more of a nare or mouth. In some embodiments, the delivering delivers gas at 1 cm or less of pressure per 10 L/min of flow. In some embodiments, the delivering delivers gas at 1 cm or less of pressure per 15 L/min of flow. In some embodiments, the subject is hypoxic or hypoxemic or hypercapnic before the method is carried out. In some embodiments, the respiratory condition is chronic obstructive pulmonary disease, asthma, pneumonia, bronchitis, or emphysema. In some embodiments, the sleep disorder is obstructive sleep apnea. In some embodiments, the method is carried out using a system of any one of claims 1 to 11.

In some configurations, a gas flow generating arrangement is disclosed which may comprise a first flow generator adapted to deliver gases at a positive flow rate, and may comprise a second flow generator adapted to draw gases at a negative flow rate. In some configurations, the gas flow generating arrangement may comprise a single flow generator configured to simultaneously deliver gases through the first gas passageway and draw gases through the second gas passageway. The flow of gases can be provided using a non-sealed or non-occluded interface. In some such configurations, the flow generator may comprise a motor. The motor may comprise a shaft. The shaft may be coupled to a first impeller and a second impeller. The motor may cause the shaft to rotate, and the first and second impellers may rotate concurrently with the shaft. The first impeller may be substantially pneumatically isolated from the second impeller. In some configurations, the first impeller may have a first housing, and the second impeller may have a second housing. In some configurations, the first and second impellers may share a single housing having individual compartments for each of the first and second impellers. The compartments may be sealed or pneumatically isolated from one another through the use of an internal partition. The respiratory therapy system may be configured such that, in use, the motion of the first impeller may deliver gases through the first gas passageway, and such that, in use, the motion of the second impeller may draw gases through the second gas passageway and may guide the gases to a flow generator outlet.

In some configurations, the first gas passageway may be in a first conduit and the second gas passageway may be in a second conduit. In some configurations, the first and second gas passageways may lie in a single conduit. The conduit may comprise a first second and a second section. The first section may accommodate the first gas passageway and the second section may accommodate the second gas passageway. The first and second sections may be pneumatically isolated from one another. The conduit may comprise a barrier. The barrier may pneumatically isolate the first and second gas passageways.

In some configurations, the first gas passageway may interface with a first patient interface and the second gas passageway may interface with a second patient interface. In some such configurations, the first patient interface may comprise a nasal interface and the second patient interface may comprise an oral interface. In some such configurations, the first patient interface may comprise an oral interface and the second patient interface may comprise a nasal interface. One or both of the first patient interface and the second patient interface may comprise a non-sealing interface.

In some configurations, the first gas passageway and the second gas passageway may interface with a patient interface that may substantially maintain pneumatic isolation of the positive and negative flows of the first gas passageway and the second gas passageway. The patient interface may comprise a non-sealing interface. The non-sealing interface may comprise a nasal cannula. The nasal cannula may comprise a first nasal prong and may comprise a second nasal prong. The first and second nasal prongs may be adapted to be fitted into the nares of the patient. The nasal cannula may comprise a manifold that may be in pneumatic communication with the nasal prongs, the first gas passageway, and the second gas passageway. In some configurations, a first side of the manifold may accept the first gas passageway, and a second side of the manifold may accept the second gas passageway. In some configurations, both the first and second gas passageways may be pneumatically linked to a single side of the manifold. In some configurations, the first gas passageway may extend into the first nasal prong, and the second gas passageway may extend into the second nasal prong. In some configurations, both the first and second gas passageways may extend into each of the first nasal prong and the second nasal prong.

In some configurations, the respiratory therapy system may comprise a humidifier. The humidifier may be adapted to heat and/or humidify gases passing through the first gas passageway. The humidifier may be positioned in-line between the gas flow generating arrangement and an airway of the patient. In some configurations, the respiratory therapy system may comprise a transfer module. The transfer module may be used to remove moisture and/or heat from the second gas passageway, and may transfer this moisture and/or heat to the first gas passageway. In some such configurations, the transfer module may comprise a wick or absorbent material. The wick or absorbent material may extend between the first gas passageway and the second gas passageway. In some such configurations, the wick or absorbent material may be present in a patient interface, e.g. a nasal cannula. In some configurations, the wick or absorbent material may be a component of the gas flow generating arrangement.

In accordance with certain features, aspects and advantages of at least one of the embodiments disclosed herein, a method of delivering gas to the airway of a subject is also disclosed. In various embodiments the method may comprise delivering gas to the airway of a subject in need thereof, improving the ventilation of a subject in need thereof, reducing the volume of anatomical dead space within the volume of the airway of a subject in need thereof, and/or treating a respiratory condition or a sleep disorder in a subject in need thereof. In various embodiments, the method may comprise delivering a continuous flow of gas to the airway of a subject, preferably at a first flow rate of at least about 10 L/min, preferably about 10 to about 60 L/min, preferably about 20 to about 40 L/min, and simultaneously drawing gas from the airway of the subject, preferably at a second flow rate that is the same as or less than or greater than the first flow rate, preferably at a second flow rate that is at least about 0.5 L/min, preferably at a second flow rate that is at least about 25% of the first flow rate, preferably at a second flow rate that is about 40 to about 60% of the first flow rate.

In various embodiments gas may be delivered to the airway of the subject through a first gas passageway and gas may be drawn from the airway of the subject through a second gas passageway that is substantially pneumatically isolated from the first gas passageway. In various embodiments the first and second gas passageways may be pneumatically connected to one or more patient interfaces that substantially maintain the pneumatic isolation of the flow of gas in each passageway. In various embodiments the first and second gas passageways may be in separate conduits or a single conduit.

In various embodiments gas may be delivered to the airway of the subject through a first patient interface and gas may be drawn from the airway of the subject through a second patient interface. In various embodiments gas may be delivered to the airway of the subject through a first patient interface and gas may be drawn from the airway of the subject through the same patient interface. In various embodiments the first patient interface may be a nasal interface and the second patient interface may be an oral interface, or the first patient interface may be an oral interface and the second patient interface may be a nasal interface. In various embodiments the first patient interface may be a nasal interface or an oral interface. In various embodiments the nasal interface may be a nasal cannula. In various embodiments the nasal cannula comprises a first nasal prong that delivers a continuous flow of gas to the airway and a second nasal prong that simultaneously draws gas from the airway, as described herein. In various embodiments the nasal cannula comprises a first nasal prong and a second nasal prong, each nasal prong delivering a continuous flow of gas to the airway and simultaneously drawing gas from the airway, as described herein. In various embodiments, a patient interface may comprise a non-sealing interface where no seal is formed at the nares and/or mouth of a subject.

In various embodiments the subject's mouth may be closed or sealed. In various embodiments the subject's mouth may be open.

In various embodiments the gas pressure in the subject's airway may be measured. In various embodiments the gas pressure in the subject's airway may be maintained at a level of less than about 4 cm H2O, preferably at a level of less than about 3.5, 3, 2.5, 5 or 1 cm H2O, preferably with the subject's mouth open or closed, preferably with the subject's mouth closed.

In various embodiments the oxygen concentration of the subject's airway may be measured. In various embodiments the oxygen concentration of the subject's airway may be maintained at a substantially constant level or increased.

In various embodiments the carbon dioxide concentration of the subject's airway may be measured. In various embodiments the carbon dioxide concentration of the subject's airway may be maintained at a substantially constant level or reduced.

In various embodiments the molar fraction of carbon dioxide in the upper airway of the subject may be reduced by at least about 10 molar % compared to the molar fraction of carbon dioxide in the upper airway of the subject when breathing without assistance. In various embodiments the molar fraction of carbon dioxide in the upper airway of the subject may be reduced by at least about 1 molar % compared to nasal high flow therapy conducted at an equivalent flow rate when the subject's mouth is open. In various embodiments the molar fraction of carbon dioxide in the upper airway of the subject may be reduced by at least about 10 molar % compared to nasal high flow therapy conducted at an equivalent flow rate when the subject's mouth is closed.

In various embodiments the peripheral capillary oxygen saturation of the subject may be measured. In various embodiments the peripheral capillary oxygen saturation of the subject may be maintained at a substantially constant level or increased. In various embodiments the peripheral capillary oxygen saturation of the subject may be increased compared to nasal high flow therapy conducted at an equivalent flow rate.

In various embodiments the method may be carried out using a system for delivering and drawing gas that is not a closed system and is vented to the surrounding atmosphere.

In various embodiments the subject may be hypoxic or hypoxemic or hypercapnic before the method is carried out.

In various embodiments the respiratory condition may be chronic obstructive pulmonary disease, asthma, pneumonia, bronchitis, or emphysema.

In various embodiments the sleep disorder may be obstructive sleep apnea.

In various embodiments the method may be carried out using a system described herein.

BRIEF DESCRIPTION OF THE DRAWINGS

Specific embodiments and modifications thereof will become apparent to those skilled in the art from the detailed description herein having reference to the figures that follow, of which.

DETAILED DESCRIPTION

Figure 1A:
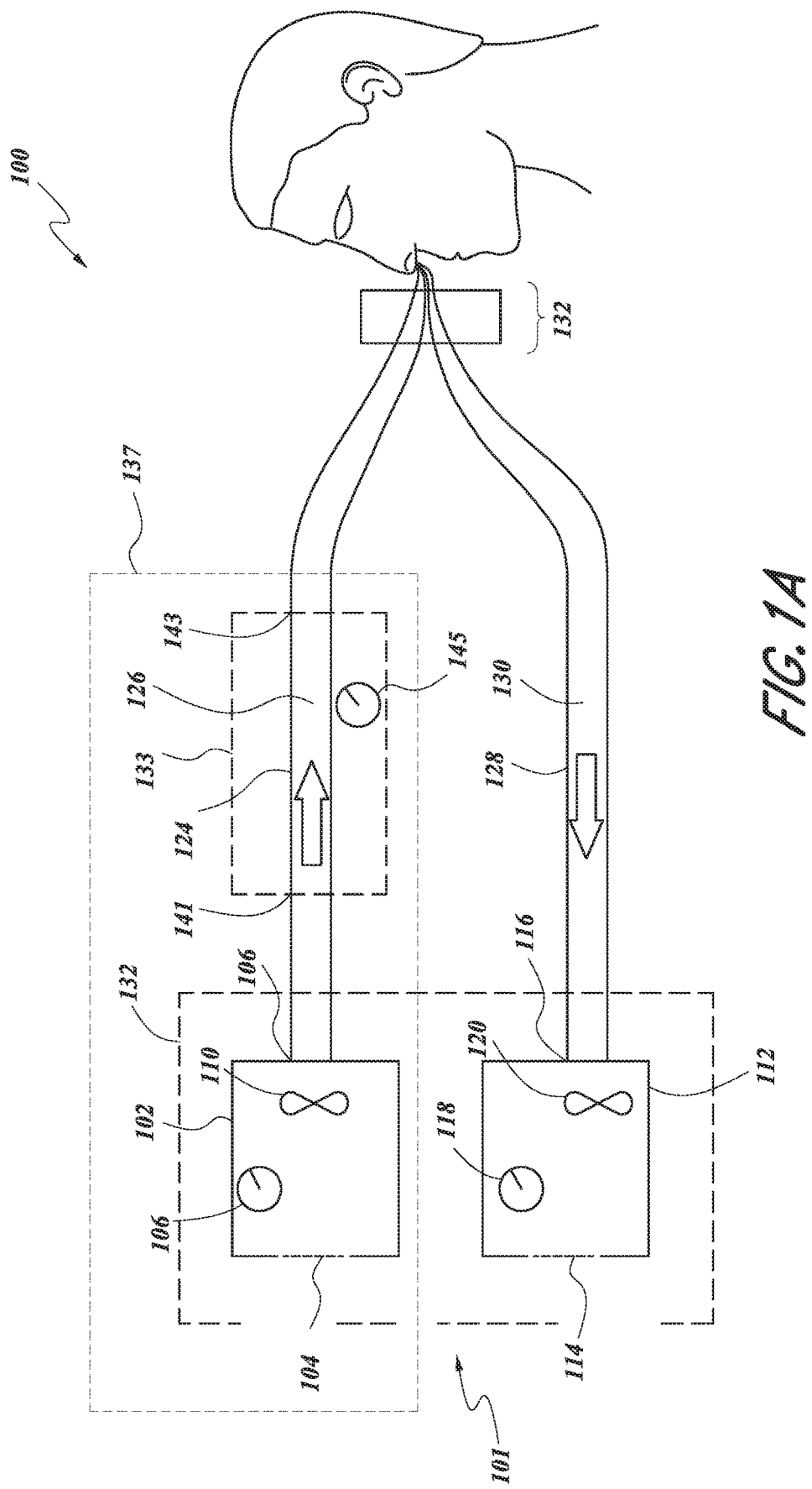
FIG. 1A is a diagram of a respiratory therapy system demonstrating certain features, aspects and advantages of some configurations of the present disclosure.

Certain features, aspects and advantages of at least one of the configurations disclosed herein include the realization that a non-sealed respiratory therapy system may be configured such that a positive gas flow may be delivered to an airway of a patient and a negative gas flow may be drawn from an airway of a patient, wherein the respiratory therapy system may be configured to simultaneously generate both the positive and negative gas flows. 'Positive flow,' 'positive gas flow,' 'positive flow rate,' or other similar or derivative phrases as referenced in this disclosure may be interpreted to refer to gas flow that substantially progresses in a direction towards an airway of the patient. 'Negative flow,' 'negative gas flow,' 'negative flow rate,' or other similar or derivative phrases as referenced in this disclosure may be interpreted to refer to gas flow that substantially progresses in a direction away from an airway of the patient. 'Non-sealed,' 'unsealed,' 'non-occluded,' 'unoccluded,' or other similar or derivative phrases as referenced in this disclosure may be interpreted to refer to a system that allows for gas exchange with ambient air in order to provide high flow rates at relatively low pressures. A further explanation of such a system is provided below.

With reference to FIG. 1, a configuration for a respiratory therapy system 100 is shown. In the illustrated configuration, the respiratory therapy system 100 may comprise a gas flow generating arrangement 101. The gas flow generating arrangement 101 may be configured to generate a positive gas flow and a negative gas flow. The gas flow generating arrangement 101 may be configured to simultaneously generate a positive gas flow and a negative gas flow. The gas flow generating arrangement 101 may comprise a first flow generator 102 configured to generate a positive flow. The first flow generator 102 may comprise a first gas inlet 104 and a first gas outlet 106. The first flow generator 102 may comprise a first blower 110. The first blower 110 may comprise a motor. The motor may comprise a stator and a rotor. The rotor may comprise a shaft. An impeller may be linked to the shaft. In use, the impeller may rotate concurrently with the shaft to draw in gas from the first gas inlet 104. The first flow generator 102 may comprise a user interface 108, which may comprise one or more buttons, knobs, dials, switches, levers, touch screens, speakers, displays, and/or other input or output modules that a user might use to input commands into the first flow generator 102 to view data and/or control its operation and/or the operation of other aspects of the respiratory therapy system 100. Operation of the first flow generator 102 may result in the generation of a positive flow of gas that may exit the first flow generator 102 through the first gas outlet 106. The gas may move along a first gas passageway 126 that may extend from the first flow generator 102 to an airway of the patient. The first gas passageway 126 may be in a first conduit 124. Optionally, a humidifier 133 may be located along the first gas passageway 126. The humidifier 133 may comprise a humidifier inlet 141 and a humidifier outlet 143. The humidifier 133 may comprise water or another moisturizing agent (hereinafter referred to as water). The humidifier 133 may comprise a heating element (not shown). The heating element may be used to heat the water in the humidifier 133 to encourage water vaporization and/or entrainment in the gas flow and/or increase the temperature and/or humidity of gases passing through the humidifier 133. The humidifier 133 may comprise a user interface 145 which may comprise one or more buttons, knobs, dials, switches, levers, touch screens, speakers, displays and/or other input or output modules that a user might use to input commands into the humidifier 133 to view data and/or control its operation and/or the operation of other aspects of the respiratory therapy system 100. The first conduit 124 may comprise a heater. The heater may be used to add heat to gases passing through the first conduit 124. The heat may prevent the condensation of water entrained in the gas stream along a wall of the first conduit 124. This heat may be useful if, for example, the humidifier 133 is utilized. The heater may comprise one or more resistive wires located in, on, around or near a wall of the first conduit 124. Gas passing through the first gas passageway 126 may be passed to a patient interface 132. The patient interface 132 may comprise a non-sealing interface. As demonstrated in FIG. 1A, the patient interface 132 may comprise a nasal cannula. However, the patient interface 132 may comprise other interfaces, including but not limited to nasal mask, an oral mask, an oro-nasal mask, a full face mask, a nasal pillows mask, a nasal cannula, an endotracheal tube, a nasogastric tube, a combination of the above or some other gas conveying apparatus or system.

A sealed nasal interface is an interface which substantially occludes a respiratory opening of a patient, such as one or more nares and/or the mouth such that either or both of inhalation and/or exhalation are forced through the cannula. The pressure of gasses delivered to a patient in a sealed system is substantially different than a non-sealed system, and thus the air flow dynamics are substantially different between the two systems such that the considerations applicable in a sealed system do not apply to a non-sealed system. Moreover, sealed systems are used for different types of patients suffering different types of respiratory problems than a non-sealed system.

For example, U.S. Pat. No. 7,823,588 (the '588 patent) describes a high pressure/high flow rate sealed interface system. Col. 3, lines 39-52 of the '588 patent describes creating a peak gas flow rate at the gas delivery device 222 (for example, a mask), of 60 L/min by providing a pressure of about 35 cm H2O. This type of high pressure/high flow system that includes gas pressures in the realm of 40-60 cm, can be useful for ventilated patients when delivered for short periods of time, for example during recruitment manoeuvres, but can be dangerous when delivered for anything longer than short periods of time. Moreover, sealed systems force can for exhaled gas back into the patient's lungs as opposed to flushing the exhaled air. Such systems, although useful for certain types of clinical situations, are not useable for prolonged administration.

High flow therapy, including nasal high flow therapy, is generally provided using a non-sealed or non-occlusive system in order to allow for a large flow of gases without an associated significant increase in pressure. For example, for nasal high flow therapy using an adult non-occlusive cannula delivering flows of 30, 40 and 50 L/min of humidified oxygen can generate nasopharyngeal mean gas pressures of about 1.93 cm, 2.58 cm, and 3.31 cm respectively. This is roughly about 15 litres of flow per 1 cm pressure. In a sealed or occluded system, the gas pressure for a given flow increases rapidly as the occlusion of the area of the orifice, such as a nare, becomes quite high, for example, at around 95-100% occlusion of the oriface. A non-sealed interface, on the other hand, would generate, for example, about 1 cm or less of pressure per 10-15 L/min of flow.

A non-sealing nasal prong is generally designed to provide less than 95% occlusion of the nares, and preferably less than 90% occlusion of the nares. The actual size and shape of the nasal prongs depends greatly on nare size of the patient. For example, pediatric nasal cannula prongs will be significantly smaller in size than adult nasal cannula prongs, despite providing an equivalent amount of occlusion in the nares. In some embodiments, the nasal prong is designed to provide only about 40-80% occlusion to account for potential deformation of a prong against the inner surface of the nare. This much smaller occlusion design is particularly useful for neonate designs, but is still applicable to pediatric and adult designs as well. In an embodiment, the nasal prong in an adult non-occlusive nasal cannula is about 4 mm in diameter. In other embodiment, the diameter of nasal cannula can range from about 3 mm in diameter to about 1 cm in diameter, depending on the size and shape of the nasal passages of the patient. Similar non-sealing considerations are also applicable to masks that cover the mouth and masks that cover both the mouth and nose as would be understood by a person of skill in the art from the present disclosure.

With further reference to FIG. 1A, the respiratory therapy system 100 may comprise a second flow generator 112. The second flow generator 112 may comprise a second inlet 116 and a second outlet 114. Likewise, the second flow generator 112 may comprise a second blower 120 that may comprise a motor. The motor may comprise a stator and a rotor. The rotor may comprise a shaft. An impeller may be linked to the shaft. In use, the impeller may rotate concurrently with the shaft to draw in gas from the second gas inlet 116. The second flow generator 112 may comprise a user interface 118 which may comprise one or more buttons, knobs, dials, switches, levers, touch screens, speakers, displays and/or other input or output modules that a user might use to input commands into the second flow generator 112 to view data and/or control its operation and/or the operation of other aspects of the respiratory therapy system 100. Operation of the second flow generator 112 may result in the generation of a negative flow of gas that may move from an airway of a patient and through a second gas passageway 130. The first gas passageway 126 and the second gas passageway 130 may be substantially pneumatically isolated from one another. The negative flow of gas may pass through the same interface 132 or a different patient interface. The second gas passageway 130 may be in a second conduit 128. The airway of the patient that is pneumatically linked to the second gas passageway 130 may be the same airway that is pneumatically linked to the first gas passageway 126, or may be a different airway than the airway that is pneumatically linked to the first gas passageway 126. For example, if the airways are different, the first gas passageway 126 may be pneumatically linked to a nasal airway and the second gas passageway 130 may be pneumatically linked to an oral airway, or alternatively the first gas passageway 126 may be pneumatically linked to an oral airway and the second gas passageway 130 may be pneumatically linked to a nasal airway. Operation of the second flow generator 112 may result in the generation of a negative flow of gas that may pass from an airway of the patient, pass through the second gas passageway 130, through the second gas inlet 116, and out the second gas outlet 114.

In the illustrated configuration, and as implied above, the respiratory therapy system 100 may operate as follows. Gas may be drawn into the first flow generator 102 through the first gas inlet 104 due to the rotation of an impeller of the motor of the first blower 110. Gas may then pass out of the first gas outlet 106 at a positive flow rate and through the first gas passageway 126, which may be in a first conduit 124. The gas may enter the humidifier 133 through the humidifier inlet 141. The humidifier 133 may be located along the first gas passageway 126 between the first flow generator 102 and an airway of the patient. Once in the humidifier 133, the gas may pick up moisture. Water in the humidifier 133 may be heated by the heating element, which may aid in the humidification and/or heating of the gas passing through the humidifier 133. The gas may then leave the humidifier 133 through the humidifier outlet 143 and progress further through the first gas passageway 126. Gas may then be passed to an airway of the patient, where it may be taken into a patient airway to aid in the treatment of a respiratory disorder. The gas may pass through a patient interface 132 on its way to the airway, which may be a nasal cannula. Preferably simultaneously, the second flow generator 112 may draw gases at a negative flow rate out of an airway of the patient and through the second gas passageway 130, which may be in a second conduit 128. The gases may be drawn through the second inlet 116 of the second flow generator 112 and out the second outlet 114. The airway in pneumatic communication with the second gas passageway 130 may be the same airway as the airway in pneumatic communication with the first gas passageway 126, and gases moving between the patient airway and the second flow generator 112 may pass through a patient interface, which may be the same patient interface 132 in pneumatic communication with the first gas passageway 130.

The negative flow provides for additional or alternative anatomical dead space clearance. Positive high flow therapy significantly reduces CO2 build up in anatomical dead spaces of the patient. Negative flow can also provide additional anatomical dead space clearance. When used together, a combination of positive and negative flow in a high flow therapy system provides for a greater reduction in CO2 in the anatomical dead spaces of a patient then just using positive flow. In addition, negative flow can be used to reduce the positive flow rate required to achieve a desired level of anatomical dead space clearance. For example, a certain positive flow rate used to provide a certain level of anatomical dead space clearance can be reduced by using a combination of positive and negative flow in order to achieve the same level of clearance. A lower positive flow rate, in some situations, can reduce patient discomfort that can occur from higher flow rates in a high flow therapy system.

Referring again to FIG. 1A, it should be understood that the illustrated configuration should not be taken to be limiting, and that many other configurations for the respiratory therapy system 100 are possible. In some configurations, the first flow generator 102 may, for example, comprise a source or container of compressed gas (for example, air). The container may comprise a valve that may be adjusted to control the flow of gas leaving the container. In some configurations, the first flow generator 102 may use such a source of compressed gas and/or another gas source in lieu of the first blower 110. In some configurations, the first blower 110 may be used in conjunction with another gas source. In some configurations, the first flow generator 102 may draw in atmospheric gases through the first gas inlet 106. In some configurations, the first flow generator 102 may be adapted to both draw in atmospheric gases through the first gas inlet 106 and accept other gases (for example, oxygen, nitric oxide, carbon dioxide, etc.) through the same first gas inlet 106 or a different gas inlet. In some configurations, the first flow generator 102 and the second flow generator 112 may have individual housings or may share a single housing 122. In some configurations, the first flow generator 102 and the humidifier 133, if present, may share a single housing 137. In some configurations, the first flow generator 102, the second flow generator 112, and the humidifier 133 may all share a single housing. In some configurations, the respiratory therapy system 100 may comprise a single user interface located on the first flow generator 102, the second flow generator 112, the humidifier 133, the patient interface 132, or another component of the respiratory therapy system 100. In some configurations, the operation of components of the respiratory therapy system 100 may be actuated wirelessly using a user interface located on a remote computing device, which may be a tablet, a mobile phone, a personal digital assistant, or another computing device. In some configurations, the operation of the first flow generator 102, of the second flow generator 112, of the humidifier 133, or of other components or aspects of the respiratory therapy system 100 may be controlled by a controller. The controller may comprise a microprocessor. The controller may be located in or on the first flow generator 102, the second flow generator 112, the humidifier 112, or other components of the respiratory therapy system 100 or on a remote computing device. In some configurations, multiple controllers may be used. In some configurations, the respiratory therapy system 100 may comprise one or more sensors for detecting various characteristics of gases in the respiratory therapy system 100, including pressure, flow rate, temperature, absolute humidity, relative humidity, enthalpy, oxygen concentration, breath composition and/or carbon dioxide concentration, or one or more sensors for detecting various characteristics of the patient or of the health of the patient, including heart rate, EEG signal, EKG/ECG signal, blood oxygen concentration, blood CO2 concentration, and blood glucose. One or more of the sensors may be used to aid in the control of components of the respiratory therapy system 100 through the use of a closed or open loop control system. In some configurations, there may be no user interface or a minimal user interface for components of the respiratory therapy system 100. In some such configurations, the respiratory therapy system 100 may utilize a sensor to determine if the patient is attempting to use the respiratory therapy system 100 and automatically operate (e.g., the first flow generator 102 may generate a positive flow, the second flow generator 112 may generate a negative flow, the humidifier 133 may humidify gases, etc.) according to one or more predetermined parameters if data obtained from the sensor indicates that the patient is attempting to use the respiratory therapy system 100. In some configurations, preferably, the first flow generator 102 may generate a positive flow of gas and the second flow generator 112 may simultaneously generate a negative flow of gas. In some configurations, the first flow generator 102 and the second flow generator 112 may be actuated at different times. For example, in some configurations, the first flow generator 102 may be configured to generate a positive flow of gas while the patient is inhaling, and the second flow generator 112 may be configured to generate a negative flow of gas while the patient is exhaling. The first flow generator 102 and/or the second flow generator 112 may be configured to generate pulsed positive and/or negative flows at frequencies that may be equal to, higher or lower than the patient's rate of respiration.

In some configurations, the first flow generator 102 and/or the second flow generator 112 may be configured to alternatively generate positive and negative flows. For example, the first flow generator 102 may be switchable between a positive flow mode and a negative flow mode, and likewise the second flow generator 112 may be switchable between a positive flow mode and a negative flow mode. Thus, in some such configurations, two separate positive flows or two separate negative flows may be administered to one or more airways of a patient. Furthermore, it should be understood that in some configurations the flows for the first flow generator 102 and/or the second flow generator 112 may be adjustable. For example, in some configurations, the first flow generator 102 may generate a positive gas flow at rates of about 0 to about 100 L/minute, or about 10 to about 30 L/minute. Similarly, the second flow generator 112 may generate a negative gas flow at rates of about 0 to about 100 L/minute, or about 10 to about 30 L/minute. In some configurations, the ranges of deliverable gas flow rate for each flow generator may encompass both positive and negative flow rates. For example, one or both of the flow generators may generate gas flows at rates of about −100 L to +100 L/minute (where −100 L/minute implies generation of a negative flow of 100 L/minute and +100 L/minute implies generation of a positive flow of 100 L/minute). In some configurations, the gas flow generation arrangement 101 may be configured in such a way that the positive flow rate is set to a function of the negative flow rate, e.g., the positive flow rate may be set to a value that is 2 times greater than the negative flow rate. In some configurations, if desired, one of the flow generators may be temporarily deactivated and gas therapy may proceed with only one of the flow generators active. In some configurations, the on/off state of one or more of the flow generators or the flow rates generated by one or more of the flow generators may be adjusted according to a function of one or more characteristics of the gases in the respiratory therapy system 100, of the patient, or of the health of the patient. The characteristics may include some or all of the characteristics listed above. In some such configurations, the adjustment may occur automatically. In some such configurations, the respiratory therapy system 100 may instead suggest adjustments (for example, through a user interface) that may be selected or confirmed by a user of the respiratory therapy system. In some configurations, more than one flow generator may be utilized to generate a positive flow or to generate a negative flow. In some configurations, a flow generator may be used together with a single gas passageway, where the flow generator may be configured to alternatively generate positive and negative flows. The delivery of positive and negative flows may be synchronized with the patient's respiratory cycle. For example, the flow generator may generate a positive flow during at least a portion of an inspiratory period and may generate a negative flow during at least a portion of an expiratory period.

Figure 1B:
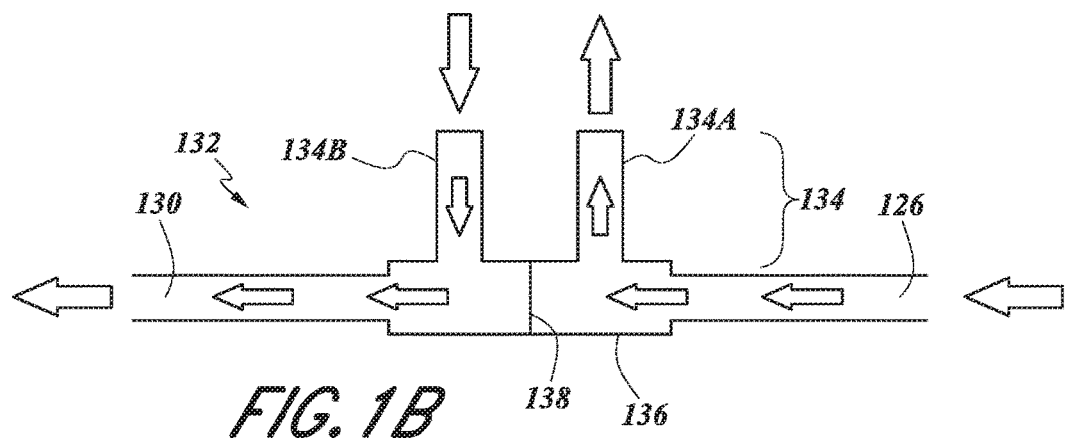
FIG. 1B depicts a nasal cannula configuration.

Attention is given towards various configurations of the respiratory therapy system 100 where a patient interface 132 in pneumatic communication with a nasal airway of the patient is used. The patient interface 132 may be a nasal cannula 132. FIGS. 1B-1M demonstrate various configurations in which a nasal cannula 132 is used with the respiratory therapy system 100. It should be understood that the nasal cannula illustrated should not be taken to be limiting, and that other cannula configurations may be utilized. For example, in some configurations, a nasal cannula with two left prongs and one right prong may be used, and/or the prongs used may have different lengths, and/or the prongs may have different orientations (for example, one prong may at least partially extend up along an internal surface of a nare and another prong may not substantially extend along an internal surface of a nare). FIG. 1B illustrates a nasal cannula 132 comprising a pronged section 134 and a manifold 136. The pronged section 134 may comprise a first nasal prong 134A and a second nasal prong 134B. A barrier 138 may be used to substantially pneumatically isolate sections of the nasal cannula 132. Gases passing through the first gas passageway 126 may enter the nasal cannula 132 through a side of the manifold 136 and enter the nasal airway of the patient through the first nasal prong 134A. Gases may also be drawn out of the nasal airway of the patient through the second nasal prong 134B and leave another side of the manifold 136 through the second gas passageway 130. The barrier 138 may aid in substantially pneumatically isolating the positive gas flow moving through the first nasal prong 134A and the negative gas flow moving through the second nasal prong 134B.

Figure 1C:
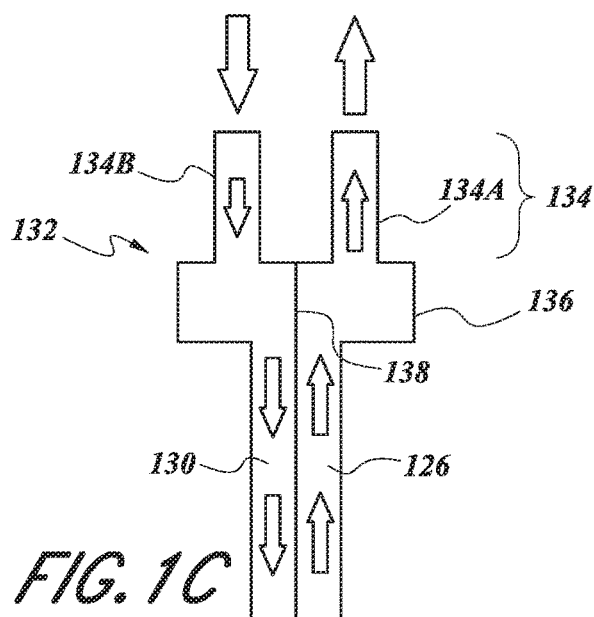
FIG. 1C depicts a nasal cannula configuration.
Figure 1D:
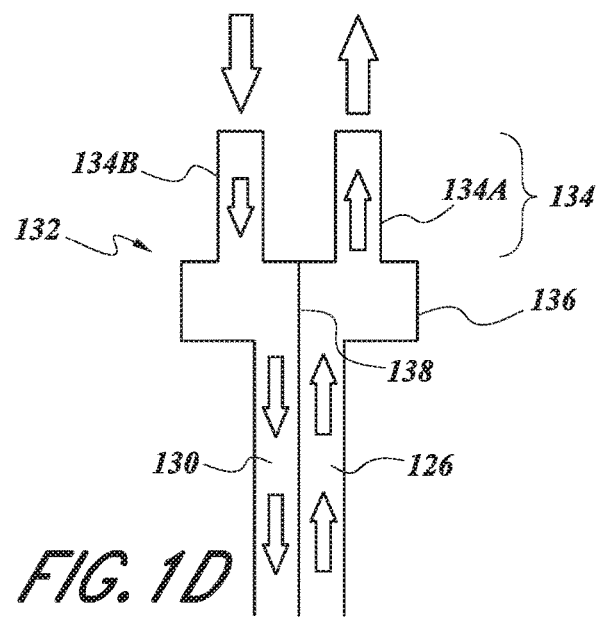
FIG. 1D depicts a nasal cannula configuration.

Although the configuration illustrated in FIG. 1B shows that the first gas passageway 126 and the second gas passageway 130 may be pneumatically linked to different sides of the manifold 136, the sides being roughly perpendicular to the nasal prongs 134A, 134B of the pronged section 134, other configurations are possible. FIG. 1C demonstrates that the first gas passageway 126 and the second gas passageway 130 may interface with the nasal cannula 132 on a single side of the manifold 136. For example, the first and second gas passageways 126, 130 may interface with the manifold 136 on a side that is roughly coaxial with the nasal prongs 134A, 134B of the pronged section 134 of the nasal cannula 132. Additionally, FIG. 1C may demonstrate that the first and second gas passageways 126, 130 may be in a single conduit. The conduit may comprise the same barrier 138 or another partition that may substantially pneumatically isolate the first and second gas passageways 126, 130. FIG. 1D may demonstrate that the first and second gas passageways 126, 130 may be in different conduits that may interface with the same side of the manifold 136. It is to be understood that the cannula examples disclosed in the present disclosure describe non-sealing interfaces as explained above. Thus, for example, the prongs 134A and/or 134B are designed such that they provide less than 95% occlusion of the nares, less than 90% occlusion or about 40%-80% occlusion of the nares as explained above in greater detail.

Figure 1E:
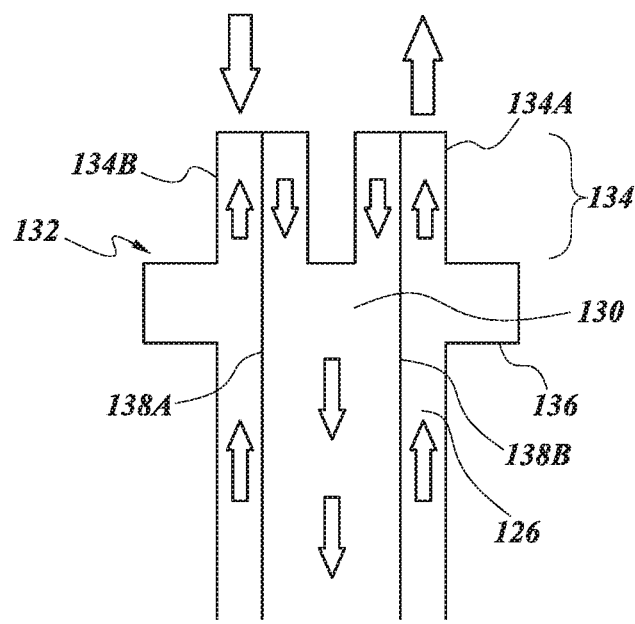
FIG. 1E depicts a nasal cannula configuration.
Figure 1F:
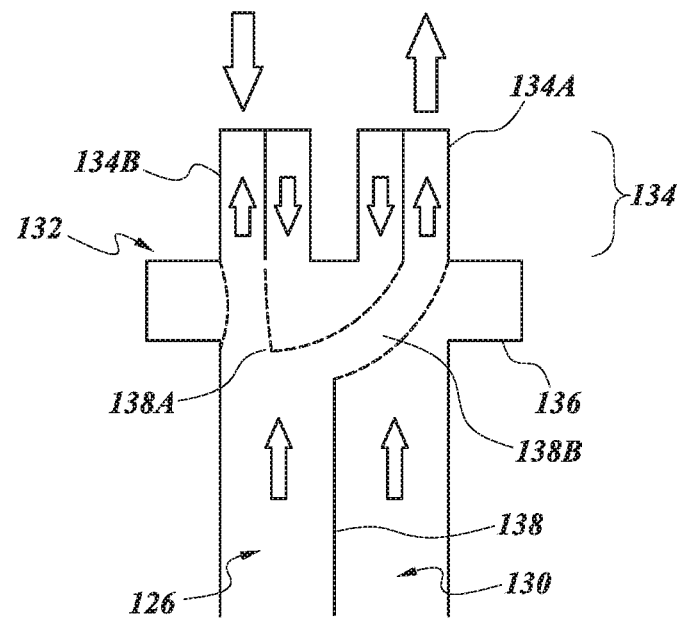
FIG. 1F depicts a nasal cannula configuration.
Figure 1G:
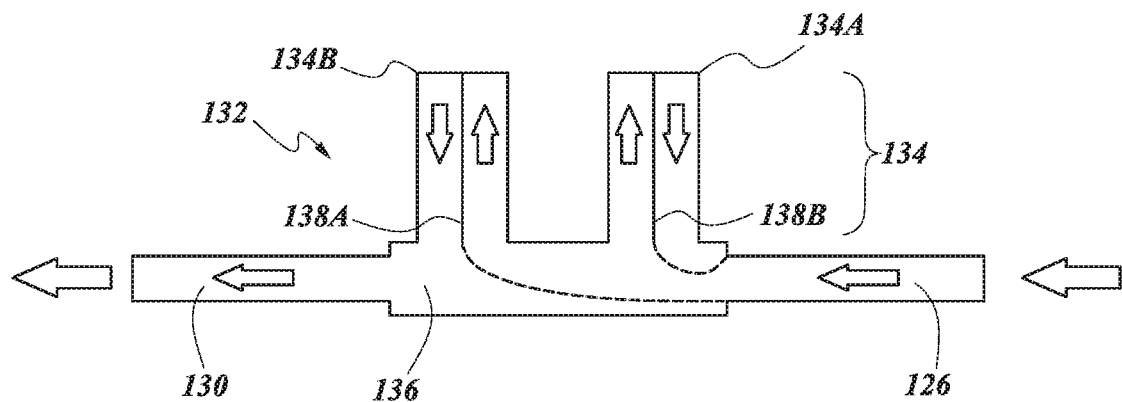
FIG. 1G depicts a nasal cannula configuration.
Figure 1H:
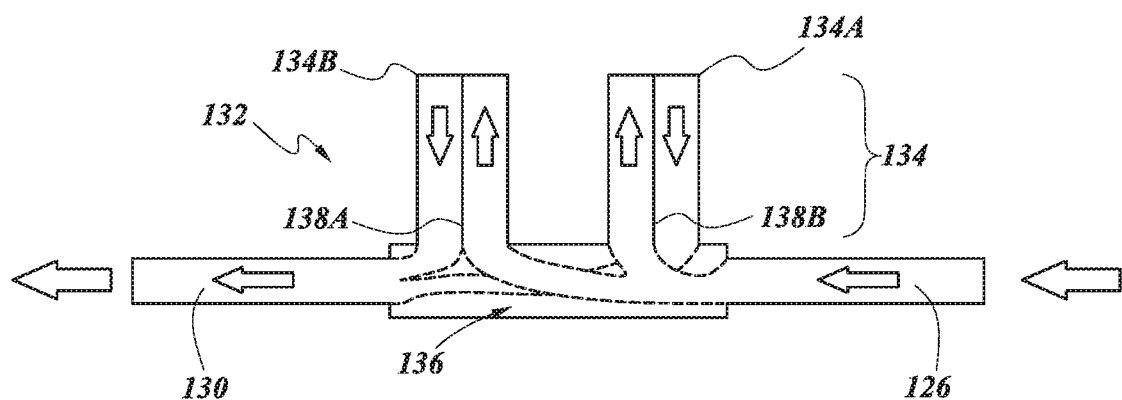
FIG. 1H depicts a nasal cannula configuration.
Figure 1I:
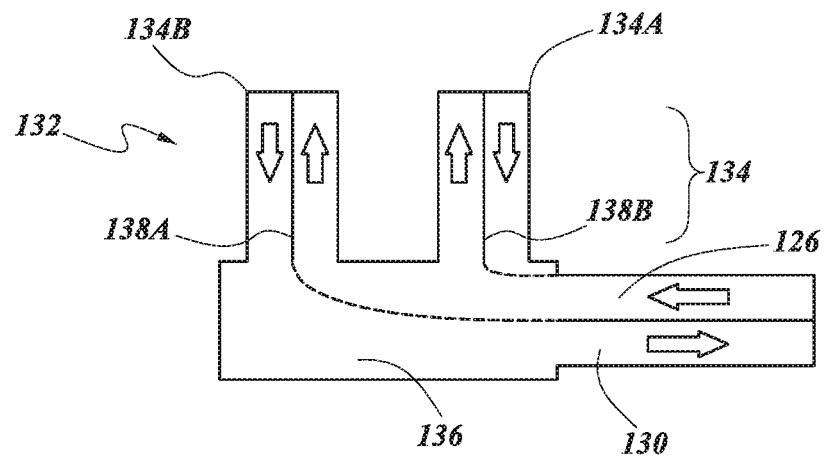
FIG. 1I depicts a nasal cannula configuration.

Advantageously, in some configurations, the respiratory therapy system 100 in combination with the nasal cannula 132 may be configured such that both positive and negative flows may be delivered/drawn with each prong 134A, 134B of the pronged section 134 of the nasal cannula 132. Similarly, preferably but not necessarily, the positive and negative flows may be administered simultaneously. The administration of both positive and negative flows in each prong 134A, 134B of the nasal cannula 132 may be more comfortable and/or more effective relative to administering a positive flow in the first prong 134A and a negative flow in the second prong 134B. As seen in FIG. 1E, the first and second gas passageways 126, 130 may be received in a single conduit interfacing with the manifold 136 that may split the positive and negative flows using a pair of barriers 138A, 138B that may extend into the prongs 134A, 134B. The flows may be split in such a way that both prongs 134A, 134B are pneumatically linked with both the positive and negative flows. FIGS. 1E and 1F demonstrate that the positive and negative flows may move in/out of the nasal cannula 132 from a single side of the manifold 136. While FIG. 1E demonstrates that a pair of barriers 138A, 138B may be used to split the flows, FIG. 1F illustrates that the first gas passageway 126 (and barrier 138) may be split at or near the manifold 136 into two compartments such that positive flow moving through the first gas passageway 126 may move into both nasal prongs 134A, 134B of the nasal cannula 132. Negative flow may be drawn out of the patient airway and through the second gas passageway 130 through the sections of the prongs 134A, 134B that are not being utilized to deliver positive flow to the patient airway. For example, the second gas passageway 130 and the nasal cannula 132 may be configured such that the negative flow of gas passes under or around the compartments that carry the positive flow of gas. Similarly, FIG. 1G demonstrates that the first and second gas passageways 126, 130 may interface with the manifold 136 of the nasal cannula 132 on different sides of the manifold 136 (e.g. on opposing sides of the manifold 136 roughly perpendicular to the prongs 134A, 134B). FIG. 1H demonstrates that each of the first gas passageway 126 and the second gas passageway 130 may be divided into compartments using, for example, the barriers 138A, 138B to deliver/draw the positive and negative flows through the nasal prongs 134A, 134B. FIG. 1I demonstrates that the first and second gas passageways 126, 130 may enter the manifold 136 of the nasal cannula 132 through a single side of the manifold 136, where the single side may be roughly perpendicular to the nasal prongs 134A, 134B of the nasal cannula 132. It should be understood that more than one of each of the positive and negative gas flows may be delivered to one or more airways of the patient (e.g. fed into each prong of the nasal cannula 132). For example, in some configurations, two negative gas flows and one positive gas flow may be used in a prong of the nasal cannula 132, or two negative gas flows and two positive gas flows may be used in a prong of the nasal cannula 132. Additionally, it should be understood that, in some configurations, the pronged section 134 may comprise only one prong adapted to be fitted into a single nare of the patient. In some configurations, the pronged section 134 may comprise more than two prongs. In some such configurations, more than one prong may be fitted into a single nare of the patient. In some configurations, one prong is larger and/or taller than the other prong. In any of the above nasal cannula 132 configurations, the positive and negative flows may be fixed or variable as implied above. Moreover, in some configurations, if more than one positive or more than one negative flow is utilized, the flow rate of each positive or negative flow may be adjusted (e.g., through a valve arrangement or some other means).

Figure 1J:
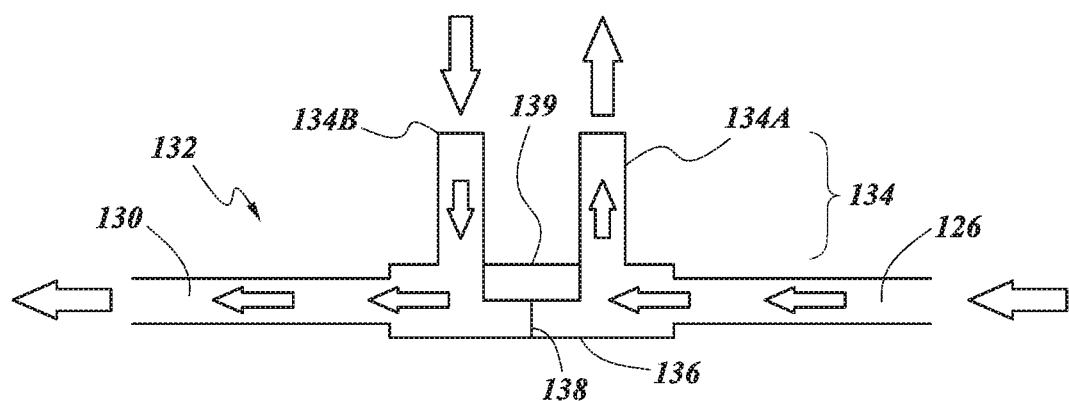
FIG. 1J depicts a nasal cannula configuration.
Figure 1K:
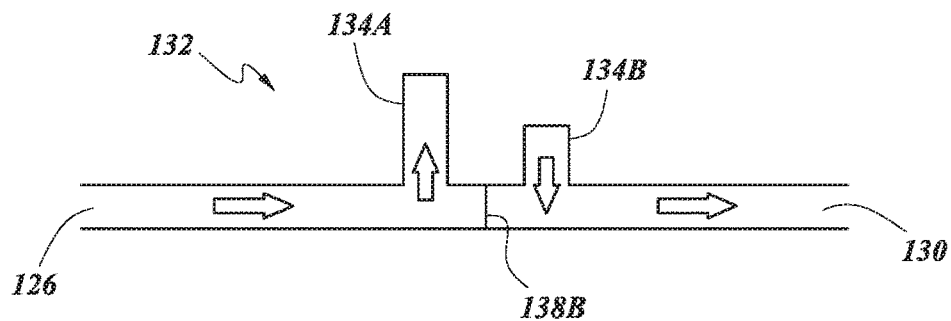
FIG. 1K depicts a nasal cannula configuration.
Figure 1L:
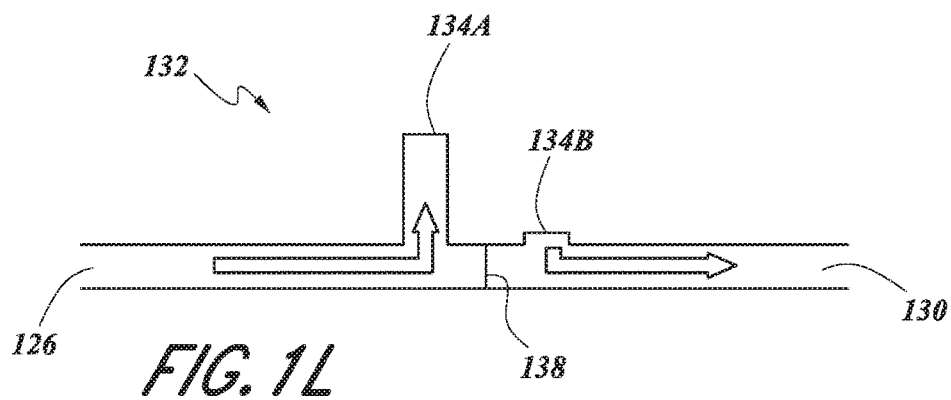
FIG. 1L depicts a nasal cannula configuration.
Figure 1M:
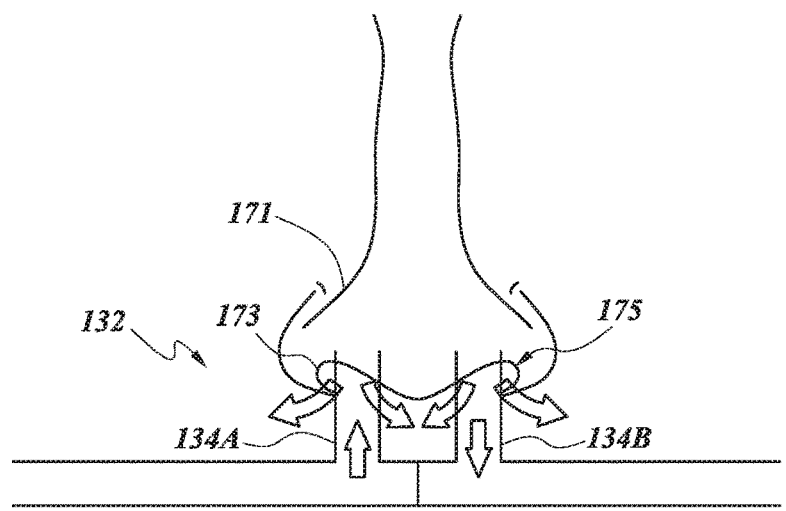
FIG. 1M depicts a non-sealed nasal cannula configuration.

In some configurations, moisture and/or heat may be removed from the negative flow of the second gas passageway 130 and added to the positive flow of the first gas passageway 126. In some such configurations, the nasal cannula 132 may comprise a transfer module 139. The transfer module 139 may be configured to aid in transferring heat and/or moisture from the negative flow (e.g. from the second gas passageway 130) to the positive flow (e.g. to the first gas passageway 126). The transfer module 139 may comprise a wick or absorbent material (hereinafter referred to as a wick). The wick may comprise, for example, natural or artificial sponge, melamine foam, metal (e.g. sodium) polyacrylates, calcium chloride, or other materials exhibiting a relatively high capacity for retaining and/or transferring heat and/or moisture. The wick may comprise anti-pathogenic materials or additives such as silver or zinc-based substances. The transfer module 139 may be positioned such that it extends between the first gas passageway 126 and the second gas passageway 130. Preferably, the transfer module 139 may act as a seal between the first gas passageway 126 and the second gas passageway 130, or may substantially prevent pneumatic communication between the first gas passageway 126 and the second gas passageway 130. FIG. 1J illustrates a nasal cannula 132 configuration in which a transfer module 139 is placed. The transfer module 139 be used to remove heat and/or moisture from exhaled/drawn gases passing through the second nasal prong 134B and through the second gas passageway 130. The heat and/or moisture may then be transferred across the transfer module 139 such that the heat and/or moisture may be entrained in the flow of gases passing through the first gas passageway 126 and into the first nasal prong 134A. FIG. 1K illustrates a nasal cannula 132 configuration in which nasal prong 134A is longer than nasal prong 134B. FIG. 1L illustrates a nasal cannula 132 in which the nasal prong 134B is removed, providing only an opening centered about the opening of the nare with negative flow. FIG. 1M illustrates a nose 171 with nares 175. The prongs 134A and 134B of cannula 132 are designed, as described above, to be non-sealing such that an exchange of air can occur at the point where the prongs 134A and 134B interact with the nares 175. This allows for a release of pressure such that a pressure build-up, either from positive or negative flow does not occur.

Figure 2A:
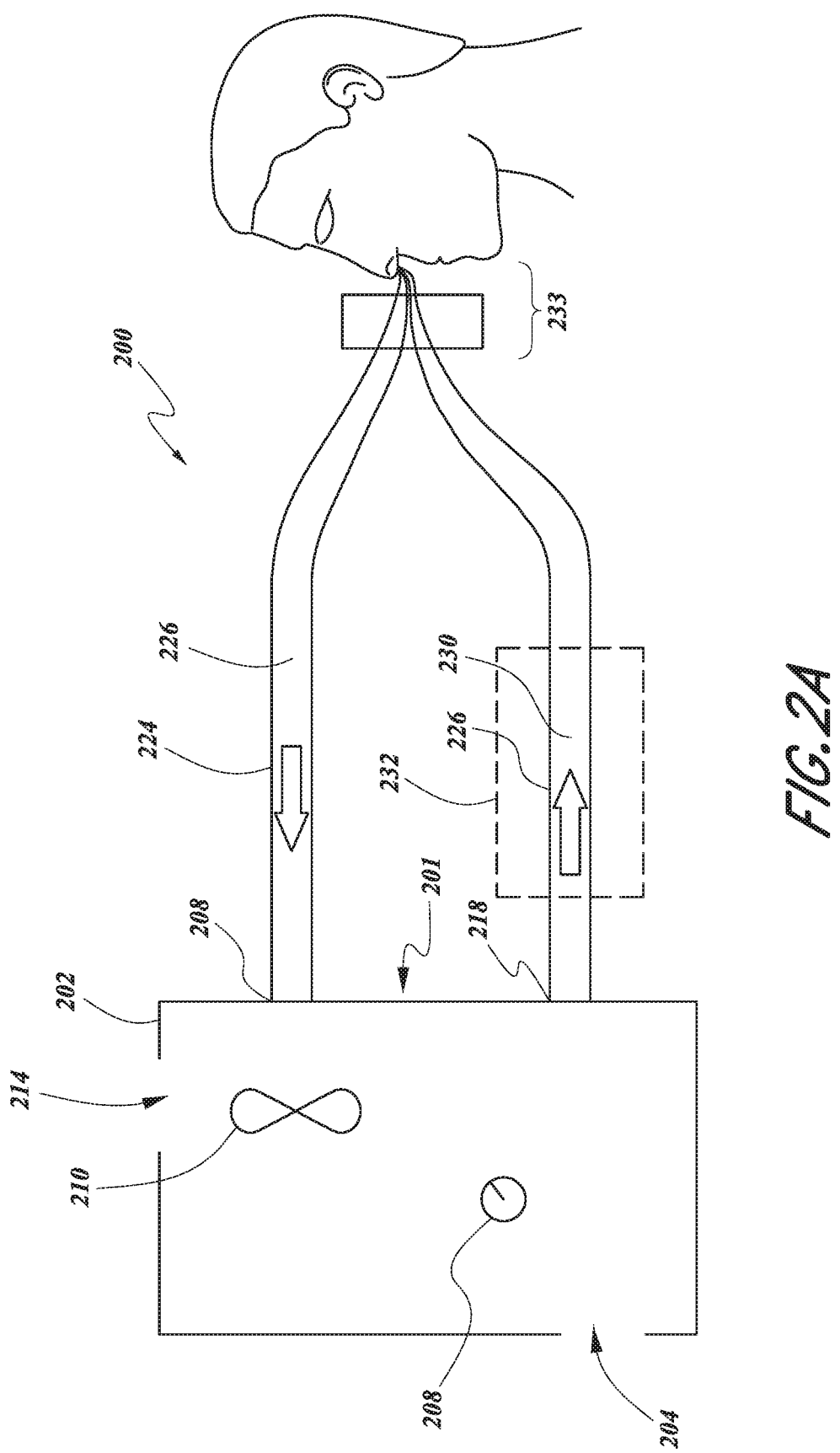
FIG. 2A is a diagram of a respiratory therapy system demonstrating certain features, aspects and advantages of some configurations of the present disclosure.
Figure 2B:
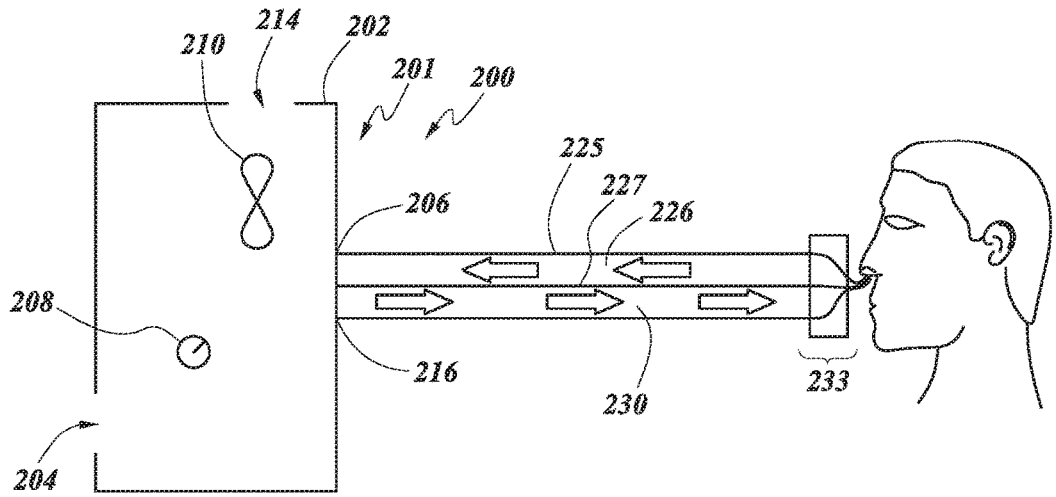
FIG. 2B is a diagram of a respiratory therapy system demonstrating certain features, aspects and advantages of some configurations of the present disclosure.

Other configurations for respiratory therapy systems capable of simultaneously delivering positive and negative flows are possible. FIG. 2A demonstrates a respiratory therapy system 200 comprising a gas flow generating arrangement 201 comprising a single flow generator 202 that may be configured to simultaneously deliver gases through a first gas outlet 216 and through a first gas passageway 230 (which may be in a first conduit 228) and draw gases through a second gas passageway 226 and through the second gas inlet 206. However, and as illustrated in FIG. 2B, it should be understood that the first and second gas passageways 230, 226 may be in a single conduit 225 that may extend between the flow generator 202 and a patient airway. The first and second gas passageways 230, 226 in the conduit 225 may be substantially pneumatically separated by a partition 227 that may lie between the first and second gas passageways 230, 226. In some configurations, the first and second gas passageways 230, 226 may be arranged such that they are in parallel (e.g. side-by-side) or arranged such that they are coaxial (e.g. one above another) with respect to one another. Similarly to the respiratory therapy system 100 of FIG. 1A as described above, the respiratory therapy system 200 may comprise a user interface 208, a first gas inlet 204, a blower 210, a gas exhaust 214 and a patient interface 233 which may comprise a non-sealing interface and which may comprise a nasal cannula. Likewise, many of the alternative configurations suggested above or elsewhere in the specification may be adapted to be used with the respiratory therapy system 200. It should be understood that in this embodiment, while they share a common gas flow generating arrangement 201, the first and second gas passageways 230, 226 are substantially pneumatically isolated from each other to the extent that the flow of gas through the first gas passageway 230 is substantially unaffected by flow of gas through the second gas passageway 226.

Figure 2C:
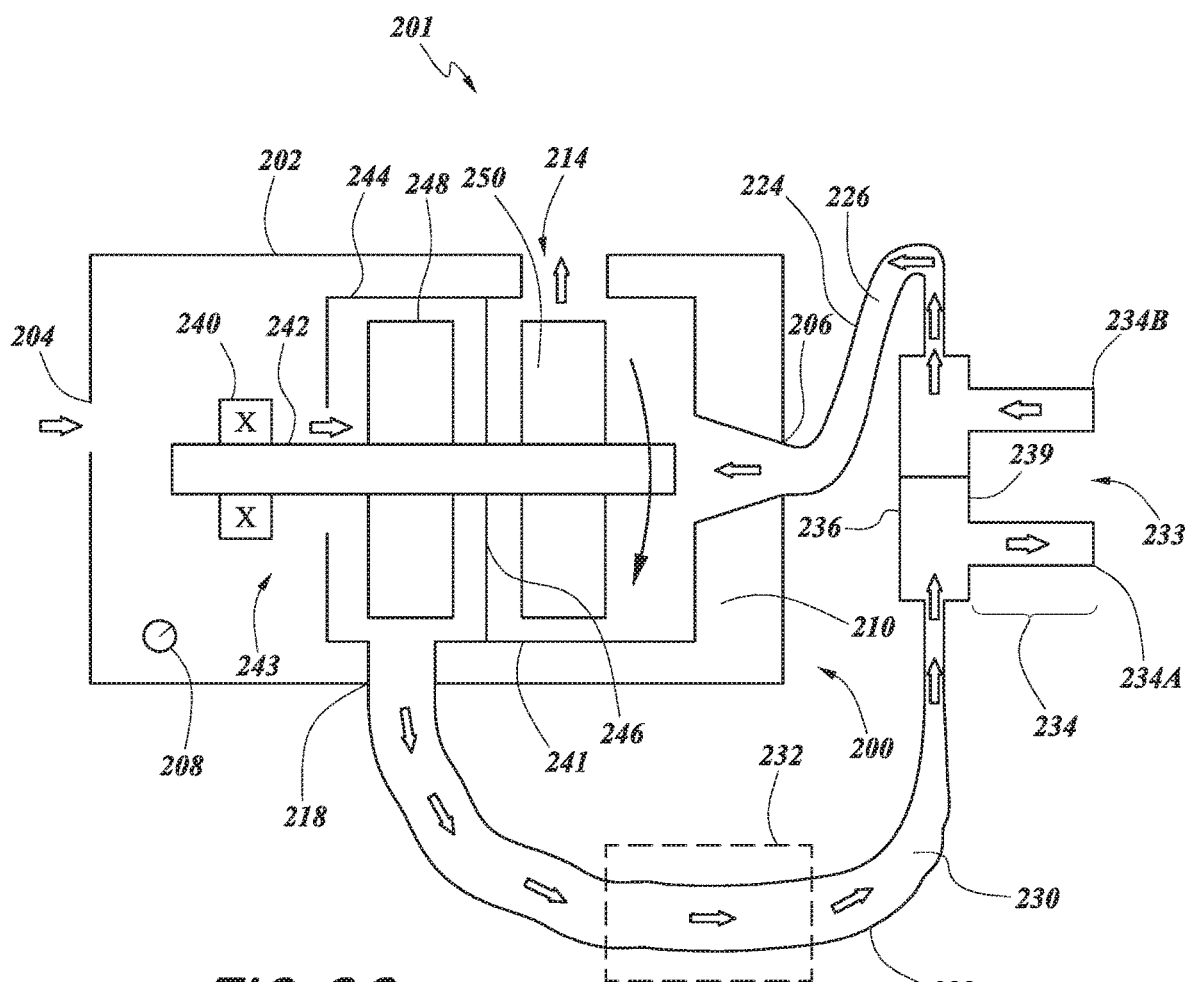
FIG. 2C is a diagram of a respiratory therapy system demonstrating certain features, aspects and advantages of some configurations of the present disclosure.
Figure 2D:
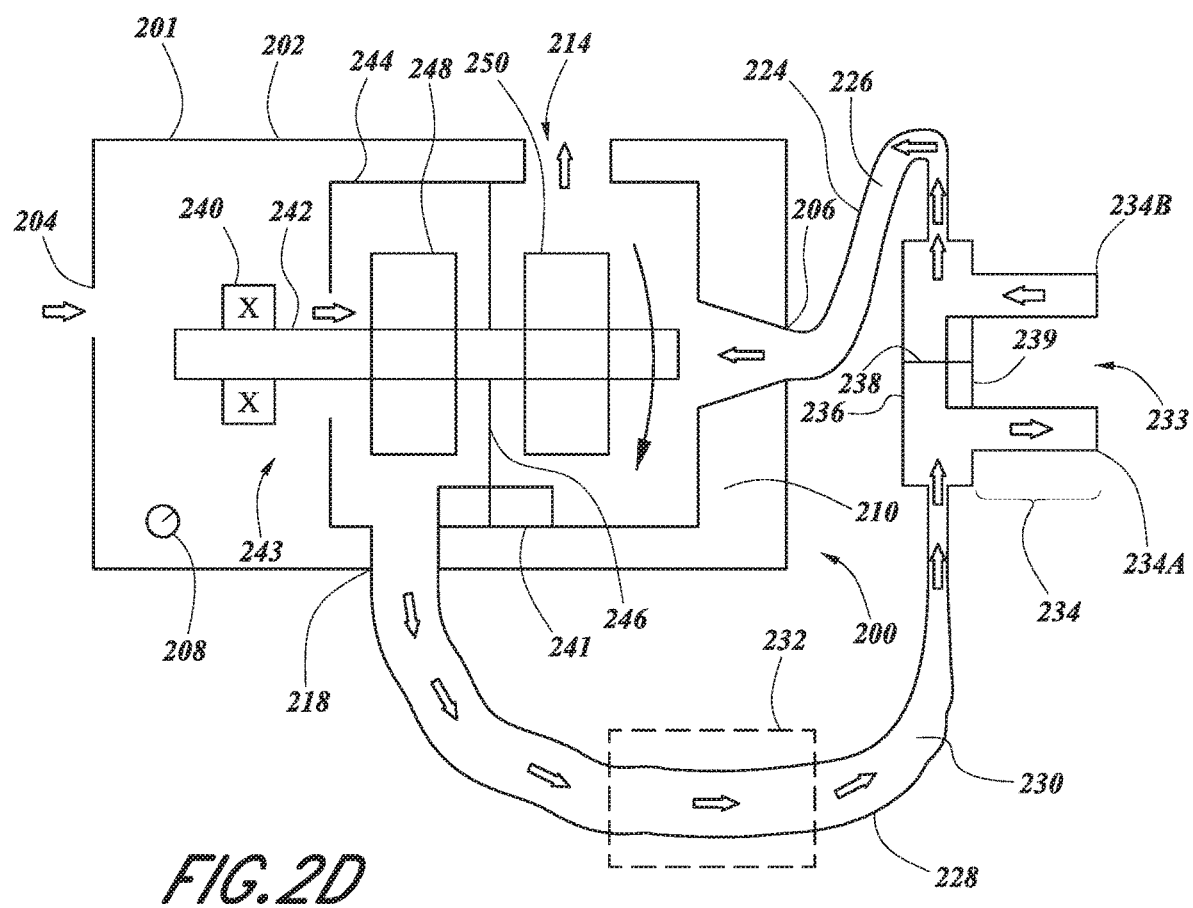
FIG. 2D is a diagram of a respiratory therapy system demonstrating certain features, aspects and advantages of some configurations of the present disclosure.

FIG. 2C demonstrates a configuration for a respiratory therapy system 200 involving a flow generating arrangement 201 comprising a flow generator 202 comprising a blower 210 capable of generating simultaneous positive and negative flows in further detail. The blower 210 may comprise a motor 243 that may comprise a stator 240 and a rotor 242. The rotor 242 may be, for example, a motor shaft. A first impeller 248 and a second impeller 250 may be coupled to the rotor 242. The first and second impellers 248, 250 may comprise a housing 244 that may pneumatically isolate the first and second impellers 248, 250. The housing 244 may comprise an internal partition 246 that may help to substantially seal or substantially pneumatically isolate the space around the first and second impellers 248, 250. In some configurations, each of the first and second impellers 248, 250 may have separate housings. In use, the concurrent rotation of the first impeller 248 with the rotor 242 due to the action of the motor 243 may cause gas to enter the blower 210 through the first gas inlet 204. Gas may be propelled out the first outlet 216 and through the first gas passageway 230 (which may pass through a humidifier 232 and which may be in a single conduit 228 as described above). The gas may be introduced into an airway of the patient using one of the interface systems demonstrated in FIGS. 1B-1H and in the above paragraphs, or using another interface or combination of interfaces. Likewise, the concurrent rotation of the second impeller 250 with the rotor 242 due to the action of the motor 243 may draw gases out of a patient airway, through the second gas passageway 226, through the second gas inlet 206 and out the gas exhaust 214. Valve arrangements may be used to further control the flows administered to the patient (e.g., the flow rates of gases passing through sections of the first gas passageway 230 and/or gases passing through sections of the second gas passageway 226). Advantageously, the use of a single blower 210 in the flow generating arrangement 201 as demonstrated in FIG. 2C may be more efficient and more cost effective than using multiple blowers. In some configurations, and as seen in FIG. 2D, the respiratory therapy system 200 may comprise a first transfer module 239 (e.g., in a patient interface) and/or a second transfer module 241 (e.g., in the blower 210, extending between the sections of the housing 244). The first transfer module 239 and/or second transfer module may be configured to aid in transferring heat and/or moisture from the negative flow (e.g., from the second gas passageway 226) to the positive flow (e.g., to the first gas passageway 230). The configurations suggested above may be equally applicable to some such transfer modules 239, 241. It should be understood that in the embodiments of FIGS. 2C and 2D, while they share a common gas flow generating arrangement 201, the first and second gas passageways 230, 226 are substantially pneumatically isolated from each other to the extent that the flow of gas through the first gas passageway 230 is substantially unaffected by flow of gas through the second gas passageway 226.

As discussed above, also disclosed herein is a method of delivering gas to the airway of a subject. In various embodiments the method may comprise delivering gas to the airway of a subject in need thereof, improving the ventilation of a subject in need thereof, reducing the volume of anatomical dead space within the volume of the airway of a subject in need thereof, and/or treating a respiratory condition or a sleep disorder in a subject in need thereof.

Figure 5:
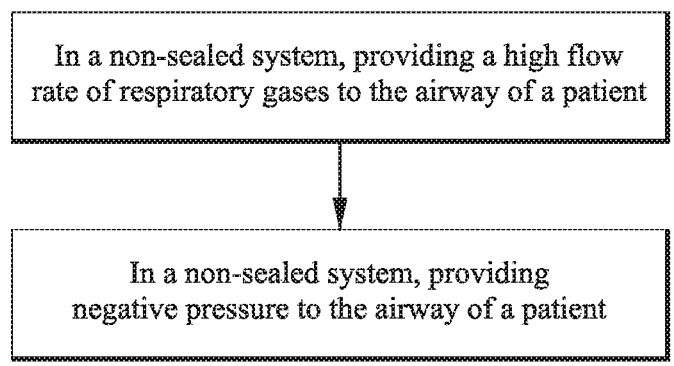
FIG. 5 illustrates a flow chart of a process for providing positive and negative high flow therapy to a patient.

For example, FIG. 5 illustrates a method of providing positive and negative flow of gases in a high flow therapy system. The method includes the step 501 of providing a positive high flow rate of respiratory gases to the airway of a patient. The method also includes the step 503 of providing negative pressure to the airway of the patient. The high flow therapy system of FIG. 5 is a non-sealed system such that pressure does not build up in the system.

In various embodiments, the method may comprise delivering a continuous flow of gas to the airway of a subject. For example, the flow of gas may be delivered at a first flow rate of at least about 10, 12, 15, 17, 20, 22, 25, 27, 30, 32, 35, 37, 40, 42, 45, 47, 50, 52, 55, 57, or 60 L/min, and useful ranges may be selected between any of these values (for example, about 10 to about 60, about 10 to about 40, or about 20 to about 40 L/min).

In various embodiments, the method may comprise simultaneously drawing gas from the airway of the subject. In some embodiments gas may be drawn from the airway of the subject at a second flow rate that is the same as or less than or greater than the first flow rate. In some embodiments the second flow rate may be at least about 5, 10, 15, 20, 25, 30, 35, 40, 45, 50, 55, 60, 65, 70, 75 or 80%, or more, of the first flow rate, and useful ranges may be selected between any of these values (for example, about 0.5 to about 80, about 35 to about 65, about 40 to about 60%). In some embodiments the second flow rate may be at least about 0.5, 1, 2, 3, 4, 5, 6, 7, 8, 9, 10, 12, 15, 17, 20, 22, 25, 27, 30, 32, 35, 37, 40, 42, 45, 47, 50, 52, 55, 57, or 60 L/min, and useful ranges may be selected between any of these values (for example, about 0.5 to about 60, about 15 to about 45, about 20 to about 40 L/min). In some embodiments the second flow rate may be about 5 to about 80% of the first flow rate, provided that the second flow rate is at least about 0.5, 1, 2, 3, 4, or 5 L/min.

In various embodiments the method may be carried out using a system as described herein or an equivalent system that is adapted to carry out the described method.

Figure 3:
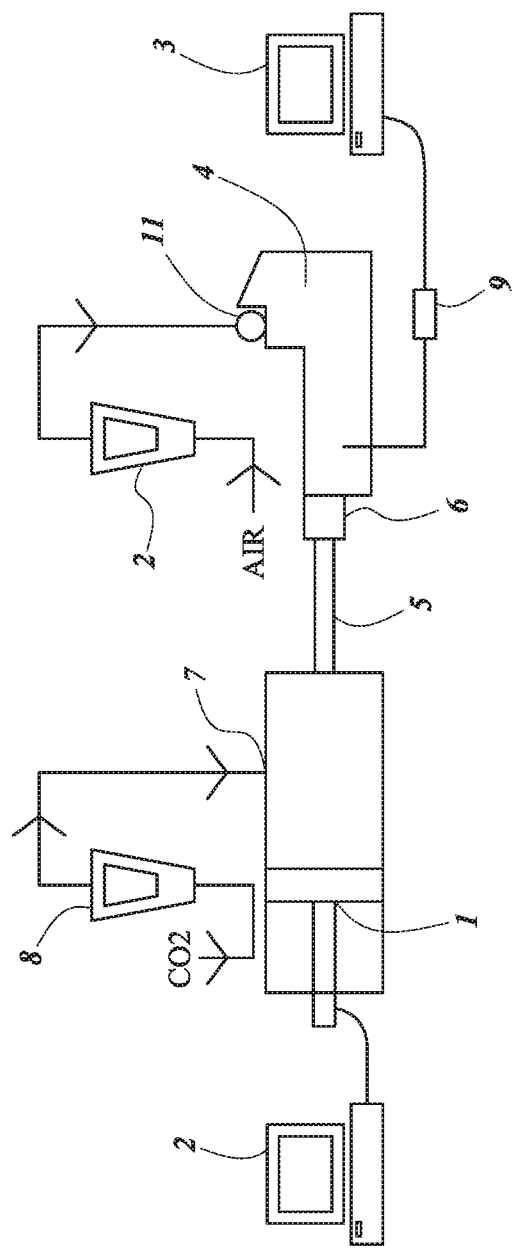
FIG. 3 is a diagram of testing apparatus useful herein.

With reference to FIG. 3, testing apparatus comprises lung pump 1, computer 2 to control pump 1 to simulate breathing, computer 3 to record sensor output, airway model 4, connecting tube 5, aluminum base block 6, CO2 bleed valve 7, CO2 rotameter 8, CO2 sensor 9, nasal high flow (NHF) rotameter 10, and NHF cannula 11.

A method and system described herein was assessed using the testing apparatus. The airway CO2 levels were assessed of (A) an untreated control model subject, (B) a model subject treated with standard NHF therapy at a flow rate of 20 L/min, (C) a model subject treated with negative NHF therapy drawing gas from the airway of the model subject using a standard two-prong nasal canula at 20 L/min, and (D) a model subject treated with an exemplary embodiment of the presently disclosed method, using negative NHF therapy drawing gas from the airway of the model subject at a flow rate of 16 L/min and positive NHF therapy simultaneously delivering gas to the airway of the model subject at a flow rate of 20 L/min, using a cannula of FIG. 1B described above. All scenarios were run with the mouth of the airway model 4 in the open position and in the closed position.

Figure 4:
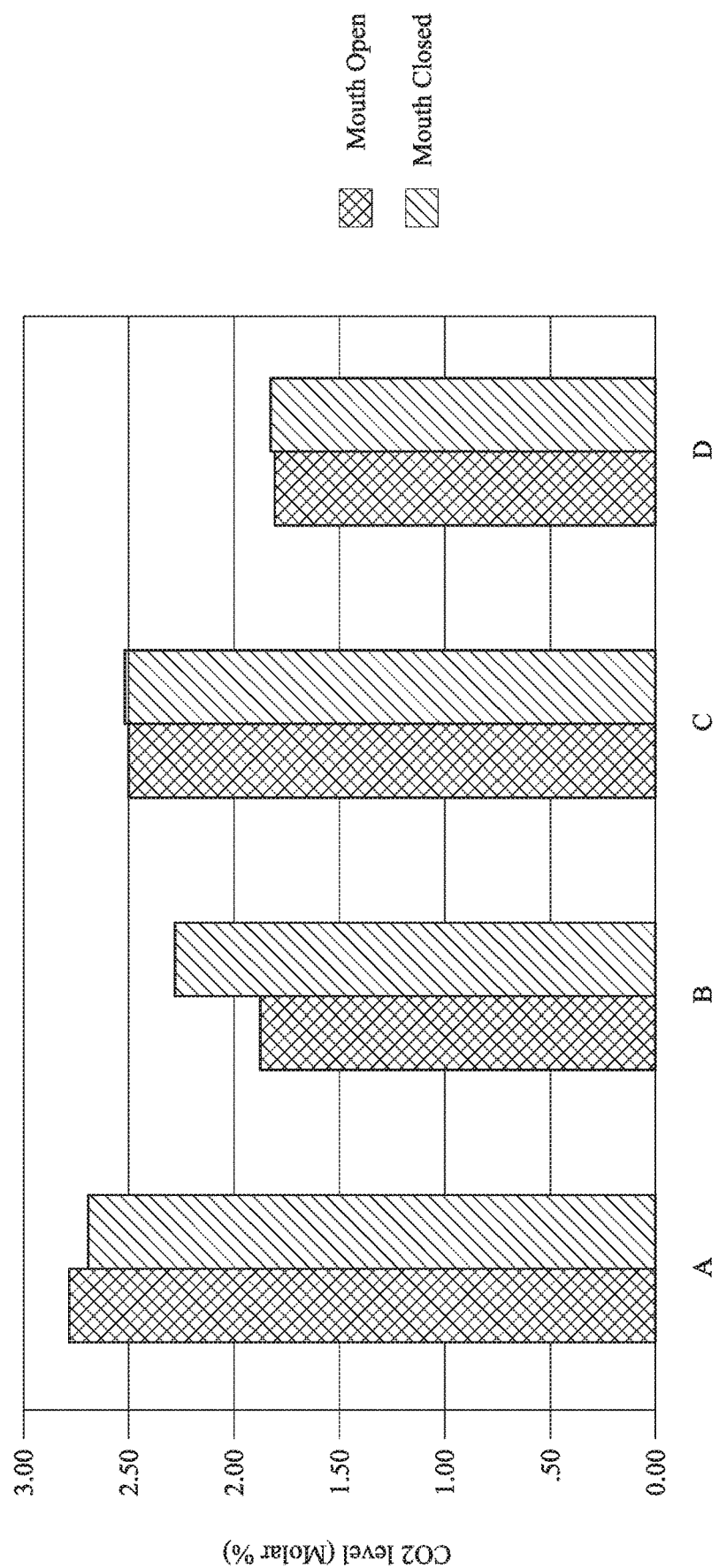
FIG. 4 is a graph of the airway CO2 level (Molar %) in (A) an untreated control model subject, (B) a model subject treated with nasal high flow therapy, (C) a model subject treated with negative nasal high flow therapy drawing gas from the airway of the model subject at 20 litres per minute, and (D) a model subject treated with an exemplary embodiment of the presently disclosed method, using negative nasal high flow therapy drawing gas from the airway of the model subject at 16 litres per minute and positive nasal high flow therapy delivering gas to the airway of the model subject at 20 litres per minute.

The results are shown in Table 1 and FIG. 4 and indicate that standard NHF therapy (B) reduced the CO2 levels in the upper airway by 32% and 14% for mouth open and mouth closed, respectively, compared to the untreated control (A). Use of negative NHF therapy (C) reduced the CO2 levels by 11% and 6% for mouth open and mouth closed, respectively, compared to the untreated control (A). Used of both negative and positive pressure (D) reduced the CO2 levels by 34% and 31% for mouth open and mouth closed, respectively, compared to the untreated control (A).

TABLE 1 results of testing

| | Average $CO_2$ level (molar %) | |
| --- | --- | --- |
| | Mouth Open | Mouth Closed |
| A | 2.83 | 2.71 |
| B | 1.91 | 2.33 |
| C | 2.52 | 2.54 |
| D | 1.85 | 1.87 |

Testing is carried out with combinations of positive and negative flow rates, including positive flow rates of from about 5 to about 60 L/min, and negative flow rates of about 5 to about 60 L/min, including specific flow rate combinations of +20/−20, +20/−40, +20/−60, +40/−20, +40/−40, +40/−60, +60/−20, +60/−40, and +60/−60 L/min.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to."

Where, in the foregoing description reference has been made to integers or components having known equivalents thereof, those integers or components are herein incorporated as if individually set forth.

The disclosed methods, apparatus and systems may also be said broadly to comprise the parts, elements and features referred to or indicated in the specification of the application, individually or collectively, in any or all combinations of two or more of said parts, elements or features.

Reference to any prior art in this specification is not, and should not be taken as, an acknowledgement or any form of suggestion that that prior art forms part of the common general knowledge in the field of endeavour in any country in the world.

Although the present disclosure has been described in terms of certain embodiments, other embodiments apparent to those of ordinary skill in the art also are within the scope of this disclosure. Thus, various changes and modifications may be made without departing from the spirit and scope of the disclosure. For instance, various components may be repositioned as desired. Moreover, not all of the features, aspects and advantages are necessarily required to practice the present disclosure. Accordingly, the scope of the present disclosure is intended to be defined only by the claims that follow.

What is claimed is:
1. A respiratory therapy system comprising:
a positive gas flow source;
a negative gas flow source;
at least one gas passageway adapted to provide a non-sealed pneumatic link between an airway of a subject and the positive and negative gas flow sources, wherein:
the at least one gas passageway comprises a first gas passageway adapted to provide a first non-sealed pneumatic link between the airway of the subject and the positive gas flow source and a second gas passageway adapted to provide a second non-sealed pneumatic link between the airway of the subject and the negative gas flow source, the first gas passageway and the second gas passageway interface with a patient interface that substantially maintains pneumatic isolation of the positive and negative flows of the first gas passageway and the second gas passageway,
the patient interface comprises a nasal cannula comprising a first nasal prong and a second nasal prong, the first and second nasal prongs adapted to be fitted into nares of the subject, and a manifold in pneumatic communication with the nasal prongs, the first gas passageway, and the second gas passageway, and
the first gas passageway extends into the first nasal prong and the second gas passageway extends into the second nasal prong; and
a hardware controller which is configured to control the positive gas flow source to deliver a continuous positive flow of gas to the airway of the subject via the at least one gas passageway and control the negative gas flow source to simultaneously provide a negative flow of gas configured to draw gas from the airway of the subject at a sufficient flow rate to reduce a concentration of an exhaled gas in a physiological dead space of the airway of the subject,
wherein the hardware controller is configured to set the rate of the negative flow of gas as a direct function of a rate of the continuous positive flow of gas, and
wherein the rate of the continuous positive flow of gas is at least 10 liters per minute.

2. The respiratory therapy system of claim 1, wherein the rate of the continuous positive flow of gas is about 20 liters per minute to about 40 liters per minute.

3. The respiratory therapy system of claim 1, wherein the rate of the negative flow of gas is at least 0.5 liters per minute.

4. The respiratory therapy system of claim 1, wherein the rate of the negative flow of gas is at least 25% of the rate of the continuous positive flow of gas.

5. The respiratory therapy system of claim 1, further comprising a wick or absorbent material configured to transfer moisture and/or heat from the second gas passageway to the first gas passageway.

6. The respiratory therapy system of claim 1, wherein the first non-sealed pneumatic link comprises an occlusion of less than 95% of the airway of the patient.

7. A method of delivering gas to an airway of a subject in need thereof, improving a ventilation of the subject in need thereof, reducing a volume of physiological dead space within a volume of the airway of the subject in need thereof, and/or treating a respiratory condition or a sleep disorder in the subject in need thereof, the method comprising:
providing a positive gas flow source;
delivering, using the positive gas flow source, a continuous flow of positive gas to the airway of a subject via at least one gas passageway adapted to provide a non-sealed pneumatic link between the airway of the subject and the positive gas flow source;
providing a negative gas flow source; and
simultaneously with the delivering of the continuous flow of positive gas, drawing gas, using the negative gas flow source, from the airway of the subject at a flow rate sufficient to reduce a concentration of an exhaled gas in the physiological dead space of the subject's airway, wherein the rate of drawing gas is set as a direct function of a rate of the continuous flow of positive gas and the rate of the continuous positive flow of gas is at least 10 liters per minute,
wherein the delivering comprises delivering via a first gas passageway adapted to provide a first non-sealed pneumatic link between the airway of the subject and the positive gas flow source and the drawing comprises drawing gas via a second gas passageway adapted to provide a second non-sealed pneumatic link between the airway of the subject and the negative gas flow source,
the first gas passageway and the second gas passageway interfacing with a patient interface that substantially maintains pneumatic isolation of the positive and negative flows of the first gas passageway and the second gas passageway, wherein the patient interface comprises a nasal cannula comprising a first nasal prong and a second nasal prong, the first and second nasal prongs adapted to be fitted into nares of the subject, and a manifold in pneumatic communication with the nasal prongs, the first gas passageway, and the second gas passageway, and
wherein the first gas passageway extends into the first nasal prong and the second gas passageway extends into the second nasal prong.

8. The method of claim 7, wherein drawing gas using the negative flow source comprises drawing gas at the rate of at least 0.5 liters per minute.

9. The method of claim 7, wherein drawing gas using the negative flow source comprises drawing gas at the rate of at least 25% of the rate of the continuous flow of positive gas.

10. The method of claim 7, wherein a gas pressure in the subject's airway is measured.

11. The method of claim 7, wherein an oxygen concentration in the subject's airway is maintained at a substantially constant level or increased.

12. The method of claim 7, wherein a carbon dioxide concentration in the subject's airway is maintained at a substantially constant level or reduced.

13. The method of claim 7, wherein a peripheral capillary oxygen saturation of the subject is measured.

14. The method of claim 7, wherein a peripheral capillary oxygen saturation of the subject is maintained at a substantially constant level or increased.

15. The method of claim 7, wherein a peripheral capillary oxygen saturation of the subject is increased compared to nasal high flow therapy conducted at an equivalent flow rate.

16. The method of claim 7, wherein the first non-sealed pneumatic link provides less than 95% occlusion of the airway of the patient.

17. The respiratory therapy system of claim 1, wherein both the first gas passageway and the second gas passageway extend into each of the first nasal prong and the second nasal prong.

18. A respiratory therapy system comprising:
a positive gas flow source;
a negative gas flow source;
at least one gas passageway adapted to provide a non-sealed pneumatic link between an airway of a subject and the positive and negative gas flow sources, wherein:
the at least one gas passageway comprises a first gas passageway adapted to provide a first non-sealed pneumatic link between the airway of the subject and the positive gas flow source and a second gas passageway adapted to provide a second non-sealed pneumatic link between the airway of the subject and the negative gas flow source, wherein the first gas passageway and the second gas passageway interface with a patient interface that substantially maintains pneumatic isolation of the positive and negative flows of the first gas passageway and the second gas passageway, the patient interface comprises a nasal cannula comprising a first nasal prong and a second nasal prong, the first and second nasal prongs adapted to be fitted into nares of the subject, and a manifold in pneumatic communication with the nasal prongs, the first gas passageway, and the second gas passageway, and both the first gas passageway and the second gas passageway extend into each of the first nasal prong and the second nasal prong; and a hardware controller which is configured to control the positive gas flow source to deliver a continuous positive flow of gas to the airway of the subject via the at least one gas passageway and control the negative gas flow source to simultaneously provide a negative flow of gas configured to draw gas from the airway of the subject at a sufficient flow rate to reduce a concentration of an exhaled gas in a physiological dead space of the airway of the subject, wherein the hardware controller is configured to set the rate of the negative flow of gas as a function of a rate of the continuous positive flow of gas, and wherein the rate of the continuous positive flow of gas is at least 10 liters per minute.

19. A method of delivering gas to an airway of a subject in need thereof, improving a ventilation of the subject in need thereof, reducing a volume of physiological dead space within a volume of the airway of the subject in need thereof, and/or treating a respiratory condition or a sleep disorder in the subject in need thereof, the method comprising:

providing a positive gas flow source;

delivering, using the positive gas flow source, a continuous flow of positive gas to the airway of a subject via at least one gas passageway adapted to provide a non-sealed pneumatic link between the airway of the subject and the positive gas flow source;

providing a negative gas flow source; and simultaneously with the delivering of the continuous flow of positive gas, drawing gas, using the negative gas flow source, from the airway of the subject at a flow rate sufficient to reduce a concentration of an exhaled gas in the physiological dead space of the subject's airway, wherein the rate of drawing gas is set as a function of a rate of the continuous flow of positive gas and the rate of the continuous positive flow of gas is at least 10 liters per minute, wherein the delivering comprises delivering via a first gas passageway adapted to provide a first non-sealed pneumatic link between the airway of the subject and the positive gas flow source and the drawing comprises drawing gas via a second gas passageway adapted to provide a second non-sealed pneumatic link between the airway of the subject and the negative gas flow source, the first gas passageway and the second gas passageway interfacing with a patient interface that substantially maintains pneumatic isolation of the positive and negative flows of the first gas passageway and the second gas passageway, wherein the patient interface comprises a nasal cannula comprising a first nasal prong and a second nasal prong, the first and second nasal prongs adapted to be fitted into nares of the subject, and a manifold in pneumatic communication with the nasal prongs, the first gas passageway, and the second gas passageway, and wherein both the first gas passageway and the second gas passageway extend into each of the first nasal prong and the second nasal prong.

* * * * *